United States Patent [19]

Hara et al.

[11] Patent Number: 5,078,150
[45] Date of Patent: Jan. 7, 1992

[54] SPECTRAL DIAGNOSING APPARATUS WITH ENDOSCOPE

[75] Inventors: Tadayoshi Hara, Hachioji; Yoichi Miyake, Sakura; Takao Tsuruoka; Kazunari Nakamura, both of Hachioji, all of Japan

[73] Assignee: Olympus Optical Co., Ltd., Tokyo, Japan

[21] Appl. No.: 346,503

[22] Filed: May 2, 1989

[30] Foreign Application Priority Data

May 2, 1988 [JP] Japan .................. 63-109736
Oct. 14, 1988 [JP] Japan .................. 63-259915

[51] Int. Cl.[5] .............................. A61B 6/00
[52] U.S. Cl. ...................... 128/665; 128/6; 128/664; 128/634; 358/98; 358/21 R
[58] Field of Search .......... 128/664, 665, 395, 4-9, 128/632-634; 358/98, 21 R, 22, 28; 356/39, 40, 41

[56] References Cited

U.S. PATENT DOCUMENTS

| 4,651,743 | 3/1987 | Stoller . | |
| 4,717,952 | 1/1988 | Kohayakawa et al. | 358/113 |
| 4,718,417 | 1/1988 | Kittrell et al. | 626/15 |
| 4,768,513 | 9/1988 | Suzuki | 128/634 |
| 4,807,026 | 2/1989 | Nishioka et al. | 128/6 |
| 4,821,117 | 4/1989 | Sekiguchi | 128/634 |
| 4,878,113 | 10/1989 | Nakamura | 128/6 |
| 4,885,634 | 12/1989 | Yabe | 358/98 |
| 4,914,512 | 4/1990 | Sekiguchi | 358/98 |

Primary Examiner—Stephen C. Pellegrino
Assistant Examiner—Robin R. Longo
Attorney, Agent, or Firm—Armstrong, Nikaido, Marmelstein, Kubovcik & Murray

[57] ABSTRACT

An object is illuminated sequentially with light of wavelengths in respective narrow bands through a light guide in an electronic endoscope provided with an imaging device. The picture images are photoelectrically converted by the imaging device and are temporarily stored respectively in memories. The spectral distribution characteristics of the object are calculated by using spectral distribution calculating data and are displayed on a display.

28 Claims, 18 Drawing Sheets

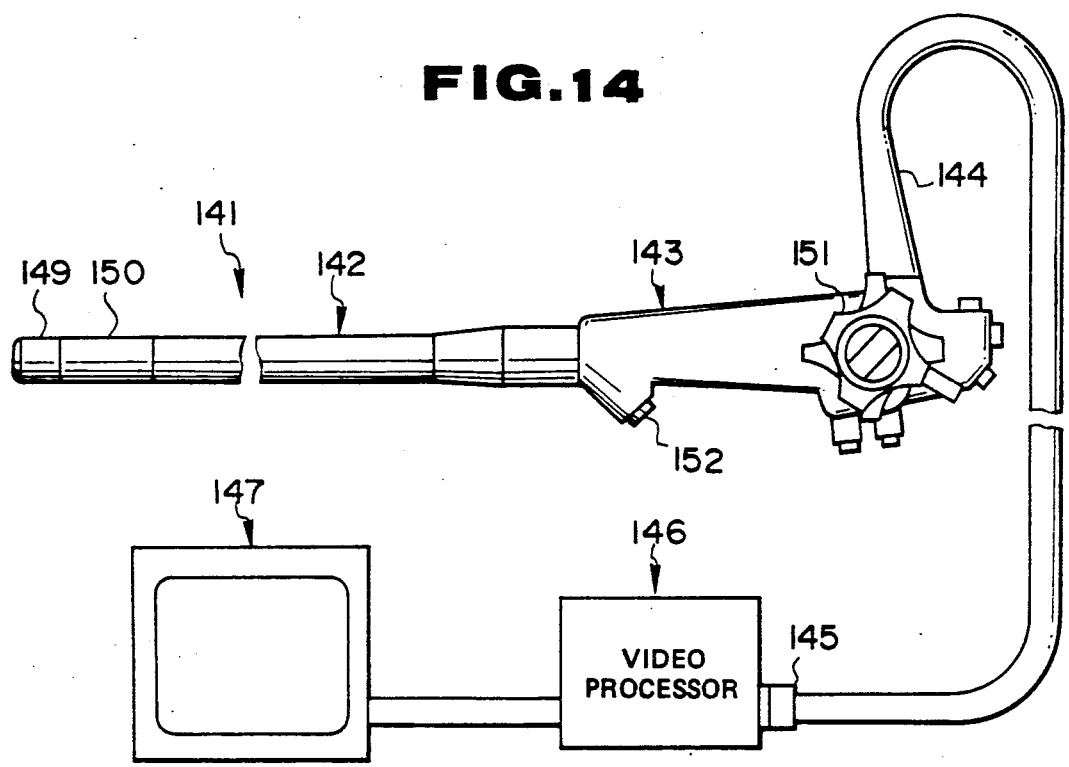
FIG. 14
FIG. 15
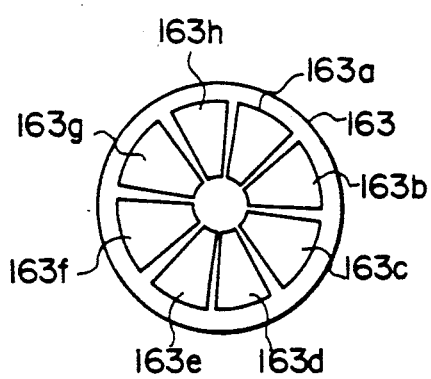
FIG. 16
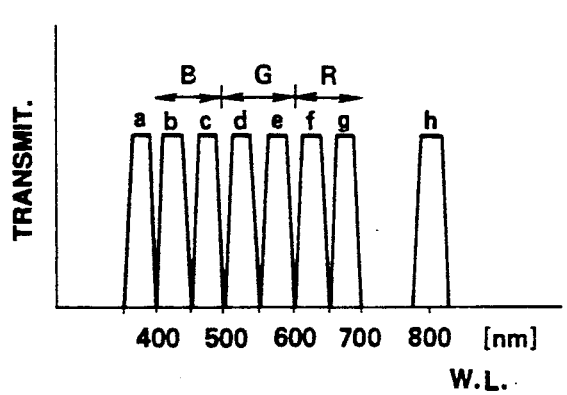

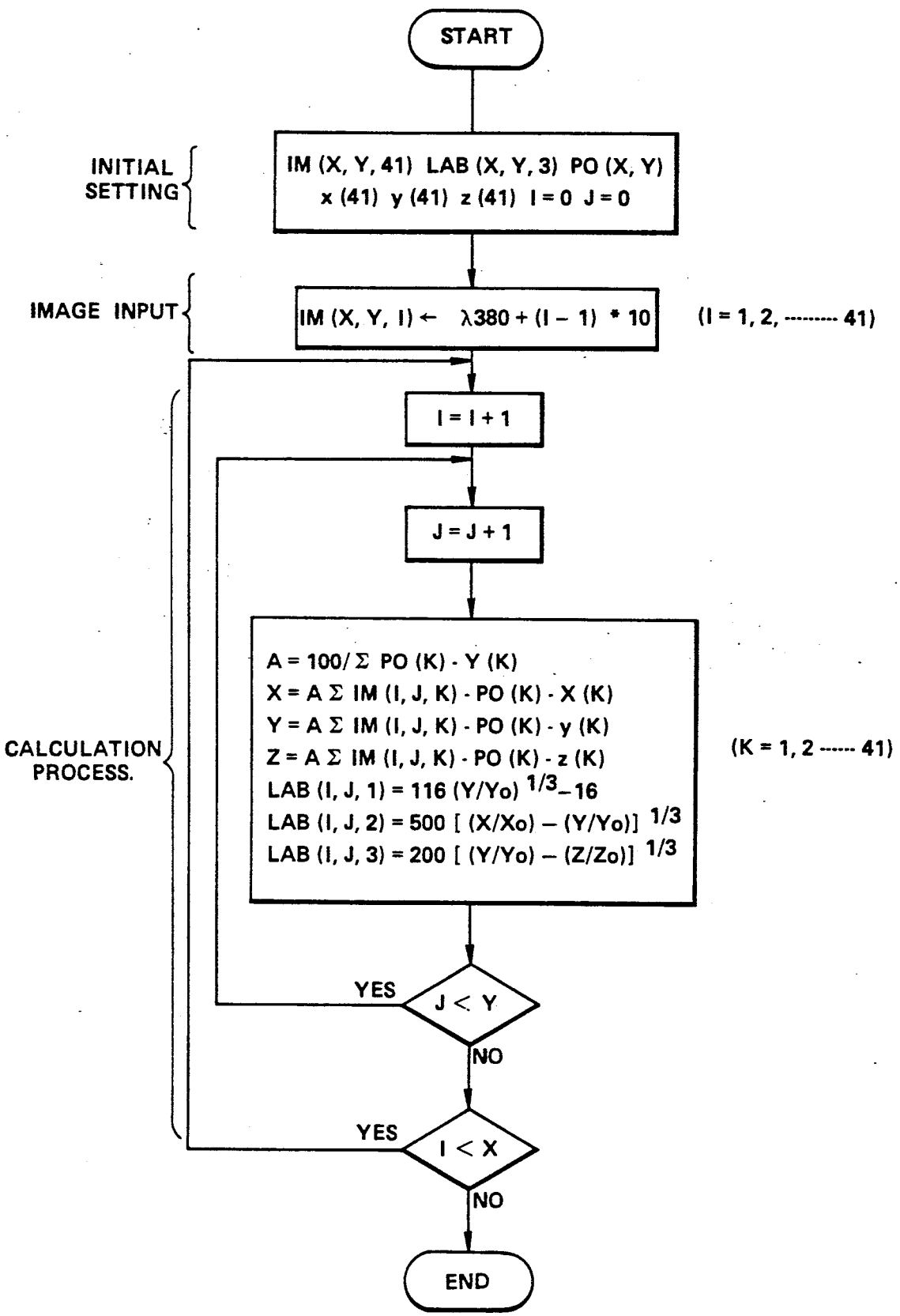

SPECTRAL DIAGNOSING APPARATUS WITH ENDOSCOPE

BACKGROUND OF THE INVENTION

1. Field of the Invention and Related Art Statement

This invention relates to a spectral diagnosing apparatus with an endoscope wherein spectral characteristics of an object are presumed by using several kinds of filters. Recently, an endoscope is extensively use whereby organs within a body cavity can be observed by inserting an elongate insertable section into a body cavity or, as required, various therapeutic treatments can be made by using treating instruments inserted through a treating instrument channel.

A conventional endoscope apparatus is of a formation as is shown in FIG. 1. As shown in FIG. 1, a conventional endoscope apparatus 201 comprises an electronic endoscope 204 whereby an elongate insertable section 203 is inserted through a body cavity of a living body 202, a video processor 206 having a video signal processing mechanism is connected to this electronic endoscope 204 through a connector 205A of a universal cord 205, a video signal color-displaying monitor 207 is connected to this video processor 206 and a sucker or aspirator 209 is connected to the electronic endoscope 4 through a cable 208 branched from the above mentioned connector 205A.

The flow of a video signal of this endoscope apparatus 201 is shown in FIG. 2. A light emitted from a lamp 211 is separated sequentially in time into respective wavelength ranges of red (R), green (G) and blue (B) by a rotary filter 213 rotated and driven by a motor 212, has the light amount regulated by a mesh filter 214 as an iris and is then incident upon the entrance end of a light guide 215 of the above mentioned electronic endoscope 204. This frame sequential illuminating light is input to the tip section of the above mentioned electronic endoscope 204 by the above mentioned light guide 215, is emitted from this tip section and is radiated to an object. The light reflected from the object from the illuminating light, is made by an imaging optical system to form an image on a CCD 221 provided in the tip section of the endoscope. A picture image signal from this CCD 221 is input into an amplifier 222 and is amplified to a voltage level in a predetermined range. The output of this amplifier 222 is input into a γ—compensating circuit 223 and isγ—compensated there. For an RGB frame sequential system, this γ—corrected signal is converted into a digital signal by an A/D converter 224 and is then stored respectively in an R memory 226R, G memory 226G and B memory 226B corresponding to the respective signals of R, G and B through a switching switch 225. The picture image signals stored in these respective memories 226R, 226G and 226B are output by the timing of a TV signal and are converted into analogue signals. The respective picture image signals converted into analogue signals are transmitted to the respective signal output ends of R, G and B together with a synchronizing signal SYNC generated by a synchronizing signal generating circuit 232. The thus obtained RGB signals are displayed on the monitor 207 shown in FIG. 1 to make an endoscope observation.

A video signal from the above mentioned amplifier 222 is input into an iris regulating mechanism section 216 consisting of an integrating circuit 217 and iris servo section 218 to regulate an exposure amount. In this iris regulating mechanism section 216, first the respective signals of R, G and B are integrated by the above mentioned integrating circuit 217 and then the integrated respective signal values are transmitted as light amount values of one picture surface to the iris servo section 218. In this iris servo section 218, the mesh filter 214 is rotated by controlling the motor 219 based on the light amount values to regulate the exposure amount.

The above mentioned electronic endoscope apparatus 201 is further provided with a controlling signal generating circuit 231 for controlling the address of the picture image signal and the timing when transmitting it. This controlling signal generating circuit 231 is connected to the above mentioned switching switch 225, respective memories 226R, 226G and 226B, synchronizing signal generating circuit 232 and motor 212 to input controlling signals to these respective elements.

Thus, in the prior art example, the visible region section is divided into three regions of R, G and B and spectral characteristics of a living body are integrated within the respective regions to form a video signal.

Therefore, minute variations in the spectral characteristics of the living body will be lost in the integrating step and it has been difficult to detect the difference between the normal part and affected part of the living body. Also, when enhancing colors, minute variations will not be able to be taken from the R, G and B signals. Therefore, it has been difficult to make a high precision treatment.

In the publication of a Japanese Patent Publication No. 55420/1982, a picture image of a specific wavelength obtained by transmitting a reflected light from an inspected object by using a half transmitting mirror, transmitting filter and reflecting mirror is obtained by an imaging tube and is processed with a color encoder to obtain a blue color picture image, green color picture image and red color picture image which are composed to obtain a picture image having a strong contrast to make it easy to distinguish the normal part and the abnormal part from each other.

In this prior art example, since all the light within the visual field is utilized for the measurement by contacting the endoscope tip section with the living body mucous membrane, no accurate data of the affected part of a size smaller than the visual field will be obtained and, since the visual field at the time of the measurement can not be secured by contacting, the record of the measured part will not be left in a photograph or the like and will not be able to be utilized later in conference or the like of the doctors themselves within the hospital. A tricolor analyzed picture image is only obtained with the half transmitting mirror or the like and a visible picture image is only made easy to see.

In a Japanese Patent Application No. 260015/1987 of the present assignee, in an electronic endoscope of a frame sequential system sequentially illuminating with a blue color light, green color light and red color light, a chromaticity value is calculated from the blue color light, green color light and red color light information of a part of the visual field and is output to a CRT to be used to determine the normal part and the abnormal part.

In this related art example, as the chromaticity value is determined by measuring and calculating colors from the electromotive force of the CCD by the blue color light, green color light and red color light of the reflected light of a part of the visual field designated on the monitor by a keyboard, in the medical treatment and diagnosis in which the variation on the adjacent boundary or the manner in the area in a range are important, each point must be measured, the diagnosing time will be long and an improvement must be made.

In U.S. Pat. No. 4,651,743, there is disclosed a method wherein different wavelengths are sequentially radiated to a tissue and the light transmitted through the tissue are sensed with a video system to obtain information relating to the tissue.

In this prior art example, as the light transmitted through the tissue are utilized, the information of only the object part can not be obtained and, by the information of the parts other than the object part, the required information will be diluted or will be made difficult to distinguish.

When using the transmitted light, the data obtained by the shape and size of the object will be different and will be difficult to utilize for diagnosis.

OBJECTS AND SUMMARY OF THE INVENTION

An object of the present invention is to provide a spectral diagnosing apparatus capable of providing two-dimensional spectral data which become an auxiliary means useful for the diagnosis of an affected part by using an endoscope.

Another object of the present invention is to provide a spectral diagnosis endoscope apparatus whereby a minute variation of spectral characteristics of a living body tissue can be detected.

In the present invention, an object to be photographed is sequentially illuminated with light of wavelengths in narrow bands, the signal of the object is photoelectrically converted by an imaging device and is temporarily stored in a memory and the picture image signal stored in the memory has the spectral distribution for the object calculated by using spectral distribution calculating data so as to be able to be used for the spectral diagnosis of the object within a short time.

BRIEF DESCRIPTION OF THE DRAWINGS

FIG. 1 is a general view of an endoscope apparatus of the prior art example.

FIG. 2 is a block diagram showing the formation of the respective sections of FIG. 1.

FIG. 3 is a formation view of a via-endoscope spectral diagnosing apparatus of the first embodiment.

FIG. 4 is an elevation showing a first rotary filter.

FIG. 5 is an elevation showing a second rotary filter.

FIG. 6 is a characteristics diagram showing a spectral transmittivity distribution of a narrow band filter provided in the second rotary filter.

FIG. 7 is a formation view of a video process circuit.

FIG. 8 is an explanatory view showing that an endoscope picture image and presumed spectral distribution are displayed in the first monitor.

FIG. 9 is a formation view of a calculating circuit calculating a spectral distribution.

FIG. 10 is a spectral distribution diagram showing the comparison of a spectral distribution in a test chart of a known reflectivity with a presumed spectral distribution determined by presumption.

FIG. 11 is a chromaticity histogram representing a presumed spectral distribution determined for all pixels in a two-dimensional histogram on a chromaticity diagram.

FIGS. 13 to 19 relate to the third embodiment of the present invention.

FIG. 13 is a block diagram showing the formation of an endoscope apparatus for spectral measurement.

FIG. 14 is a general explanatory view of an endoscope apparatus.

FIG. 15 ia an elevation of a rotary filter.

FIG. 16 is a diagram showing wavelength ranges of light transmitted by respective color transmitting filters.

FIG. 17 is a diagram showing spectral characteristics of hemoglobin.

FIG. 18 is a block diagram showing the formation of a calculating process circuit.

FIG. 19 is a flow chart showing the operation of the calculating process circuit.

FIGS. 20 to 22 relate to the fourth embodiment of the present invention.

FIG. 20 is a block diagram showing the formation of an endoscope apparatus.

FIG. 22 is an explanatory view in case the bands of R, G and B signals are moved.

FIGS. 23 to 25 relate to the fifth embodiment of the present invention.

FIG. 24 is a flow chart showing the operation of a calculating process circuit.

FIG. 25 is an explanatory view showing CIE equal color functions.

DETAILED DESCRIPTION OF PREFERRED EMBODIMENTS

Figure 1:
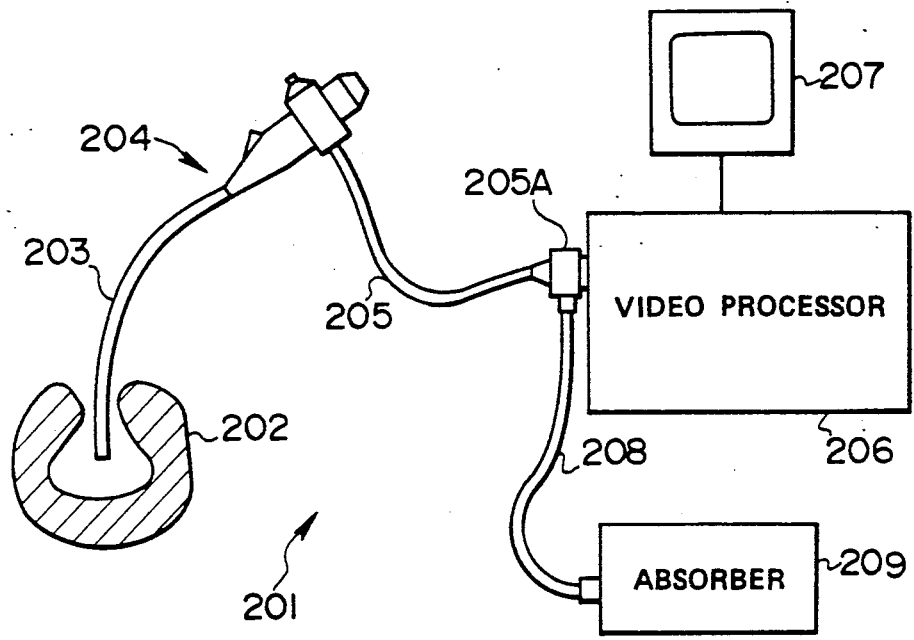
FIGS. 1 and 2 relate to a prior art example.
Figure 2:
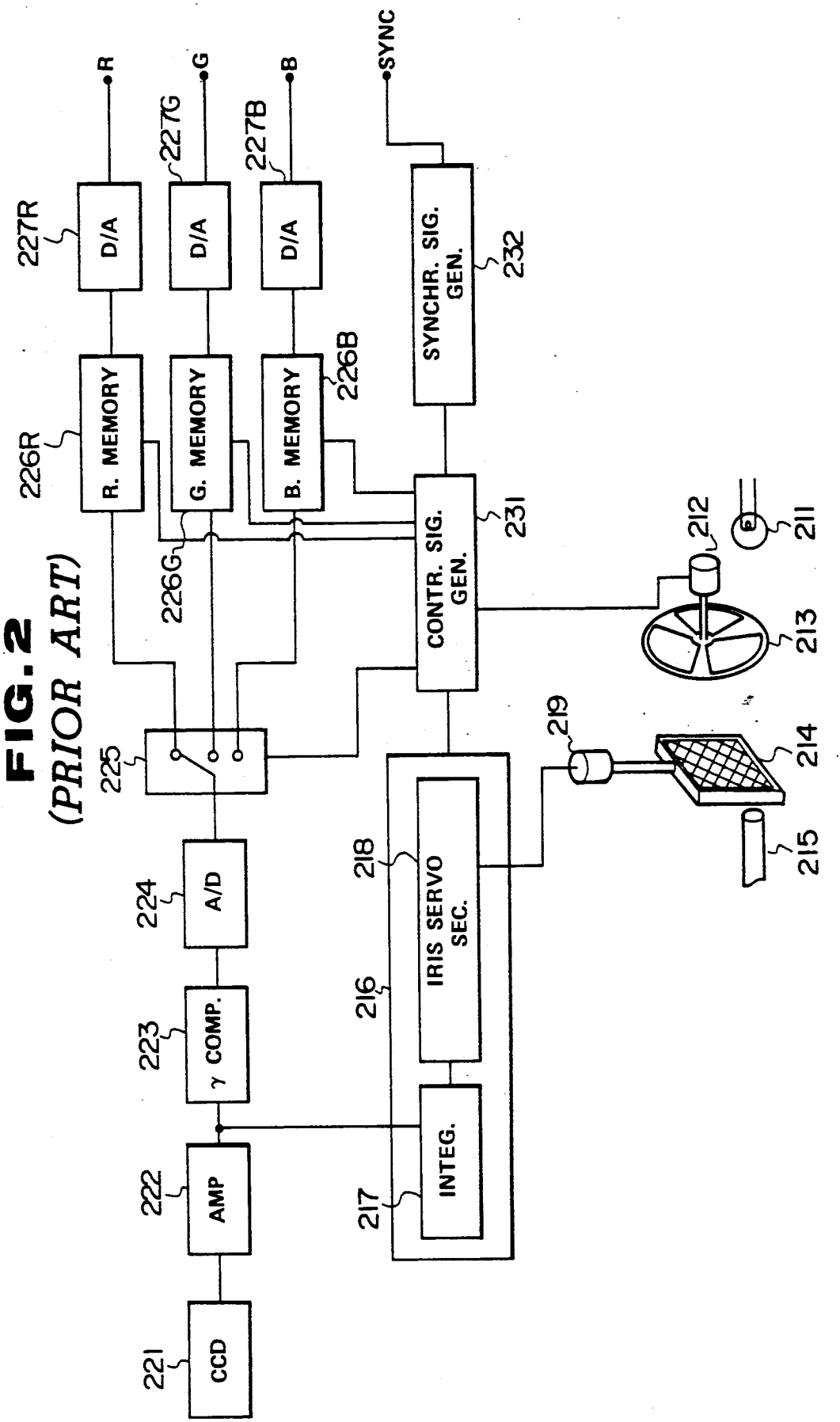
Figure 3:
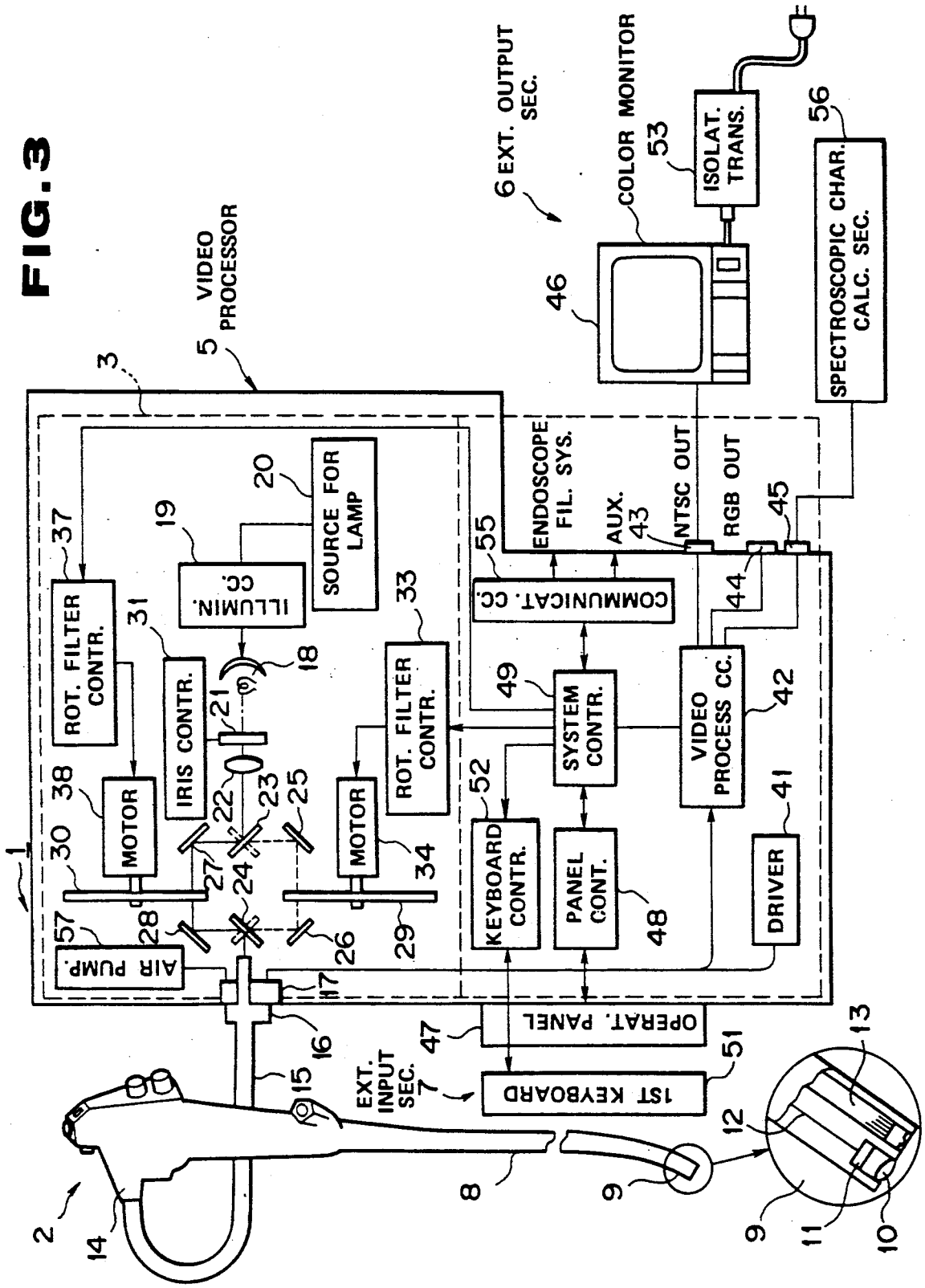
FIGS. 3 to 11 relate to the first embodiment of the present invention.

As shown in FIG. 3, a (via-endoscope spectral) diagnosing apparatus 1 of the first embodiment comprises a frame sequential type electronic scope 2, a video processor 5 containing a frame sequential type light source section 3 feeding an illuminating light to this frame sequential type electronic scope 2 and a signal processing section, an external output section 6 displaying a video signal output from this video processor 5 and displaying the spectral diagnosing result and an external input section for making the above mentioned video processor do a desired process.

The above mentioned frame sequential type electronic scope 2 has an elongate flexible insertable section 8 containing in the tip section 9 an objective lens 10 and a charge coupled device (CCD) 11 arranged in the focal plane of this objective lens 10. A signal cable 12 connected with the CCD 11 and a flexible light guide 13 transmitting an illuminating light are inserted through the insertable section 8 and are inserted through a universal cord 15 extended out of an operating section 14 so that a connector 16 fitted to this universal cord 15 at the end may be connected to a connector receptacle 17 of the video processor 5.

When the above mentioned connector 16 is connected to the connector receptacle 17, an illuminating light will be time sequentially input to the entrance end surface of the above mentioned light guide 13 from the light source section 3.

The light source section 3 within the above mentioned video processor 5 is provided with a lamp current source 20 feeding a driving electric power to a xenon lamp 18 to be a light source through a lighting circuit 19 and is provided on a light path connecting the above mentioned xenon lamp 18 and the above mentioned light guide 13 at the entrance end with an iris 21 adjusting the light amount of the xenon lamp 18, a condenser lens 22 for condensing and radiating the light having passed through this iris 21 on the entrance end surface of the light guide 13 connected to the above mentioned connector receptacle 17, movable reflecting mirrors 23 and 24 for changing the light path, fixed reflecting mirrors 25, 26 and 27, 28 respectively forming the first and second light paths for these mirrors 23 and 24 and first and second rotary filters 29 and 30 interposed on the light paths respectively between a pair of these fixed reflecting mirrors 25 and 26 and between the fixed reflecting mirrors 27 and 28.

The above mentioned iris 21 can be controlled in the diagram amount by an iris controlling circuit 31. The above mentioned movable reflecting mirrors 23 and 24 are controlled, for example, by rotary solenoids (not illustrated) in a known manner so that the mirror surfaces may be rotated and displaced by 90 degrees. These mirrors 23 and 24 are rotated and displaced as operatively connected so that, as shown in FIG. 3, in the state shown by the solid lines, the light reflected by the mirror 23 will be radiated on the entrance end surface of the light guide 13 through the fixed reflecting mirror 27, second rotary filter 30, fixed reflecting mirror 28 and movable reflecting mirror 24. When the mirrors 23 and 24 are set in the state shown by the dotted lines, the light reflected by the mirror 23 will be radiated on the entrance end surface of the light guide 13 through the mirror 25, first rotary filter 29 and mirrors 26 and 24.

Figure 4:
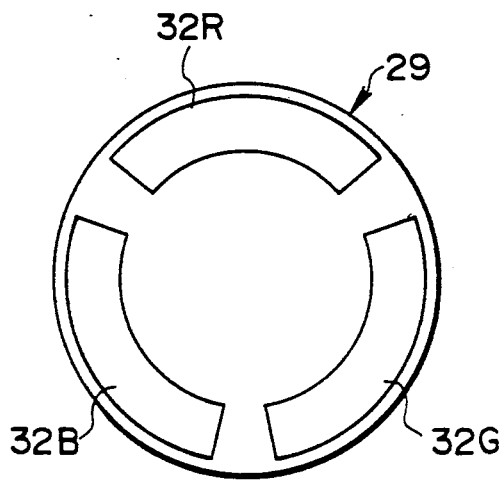

The above mentioned first rotary filter 29 is to make an ordinary frame sequential illumination and is fitted with red, green and blue color transmitting filters 32R, 32G and 32B in three sector openings provided in the peripheral direction in a light intercepting disc as shown in FIG. 4. This first rotary filter 29 is fitted to the rotary shaft of a motor 34 having the rotating speed controlled to be constant by a (first) rotary filter controller 33. Therefore, in case the above mentioned rotary reflecting mirrors 23 and 24 are set in the state shown by the dotted lines, by being passed through this first rotary filter 29, the light of the wavelengths of red, green and blue will be radiated sequentially on the entrance end of the light guide 13.

Figure 5:
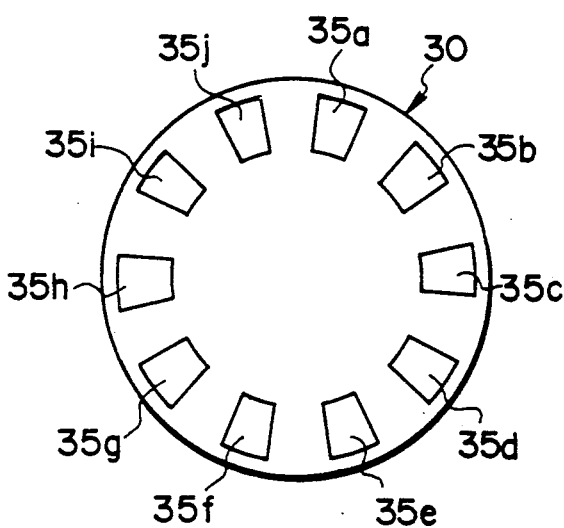

The above mentioned second rotary filter 30 is provided, for example, with ten narrow band filters 35a, 35b, 35c, 35d, 35e, 35f, 35g, 35h, 35i and 35j in the peripheral direction as shown in FIG. 5 and is fitted to the rotary shaft of a motor 38 having the speed controlled by a (second) rotary filter controller 37.

Figure 6:
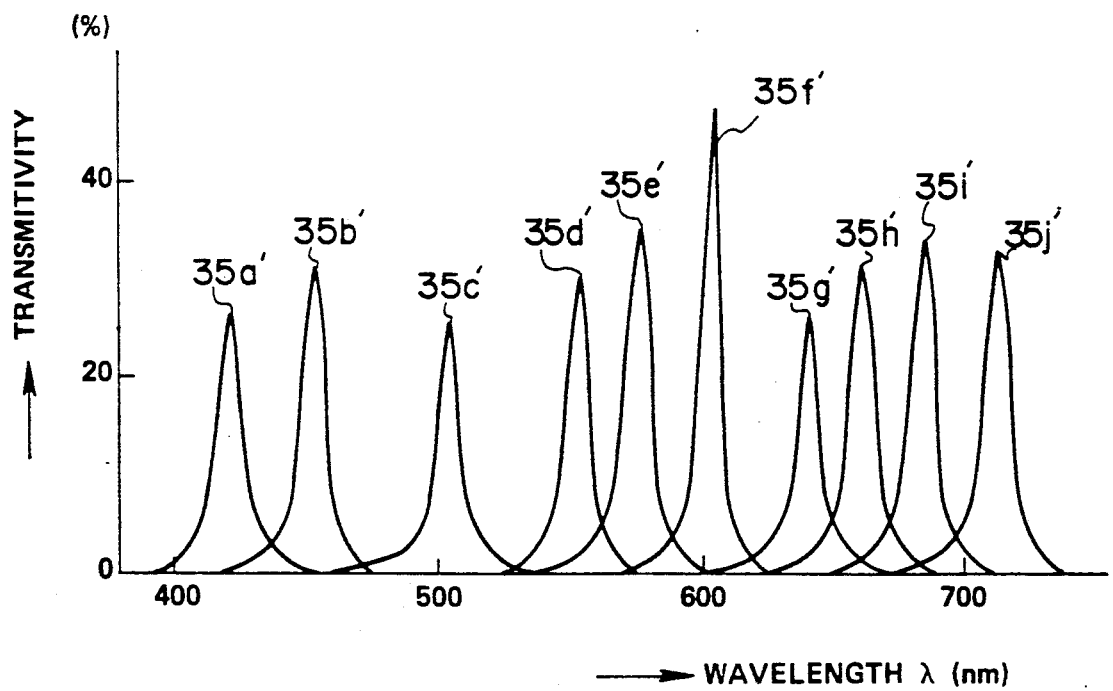

The spectral transmittivity distributions of the ten narrow band filters 35a, . . . and 35j provided in the above mentioned second rotary filter 30 are shown in FIG. 6. As clear from FIG. 6, the spectral transmittivity distributions 35k' of the respective narrow band filters k (k=a, b, . . . ) are formed respectively of the light transmitted only through the narrow wavelength bands. Therefore, when the movable reflecting mirrors 23 and 24 are set in the state shown by the solid lines in FIG. 3, the illuminating light of the narrow bands transmitted through the respective narrow band filters 35a, 35b, . . . . and 35j, that is, the wavelength light transmitted through the spectral filters of the multichannels will be radiated on the entrance end surface of the light guide 13.

The signal processing section 4 of the video processor 5 has a driver 41 driving the above mentioned CCD 11 through the above mentioned cable 12, a video process circuit 42 taking in the signal from the driven CCD 11 through the cable 12, converting it to a desired video signal and outputting it, an NTSC output terminal and RGB output terminal 44 for delivering the output of this video process circuit 42 to the above mentioned external output section 6 and also a measuring terminal 45. The first color monitor 46 is connected to either one of the NTSC output terminal 43 and RGB output terminal 44.

The above mentioned video process circuit 42 is connected with a system controller 49 connected with an operating panel 47 provided on the front surface of the video processor 5 through a panel controller 48 and making various controls.

A first keyboard 51 forming the above mentioned external output section 7 can be connected to the operating panel 47 and is electrically connected with the above mentioned system controller 49 through a keyboard controller 52 so that, by the operation of this keyboard 51, input data may be displayed in a first monitor 46 forming the above mentioned external output section 6, a measuring zone may be designated or output data may be controlled. The first color monitor 46 is input with a current source electric power through an isolated transformer 53. The above mentioned system controller 49 is electrically connected to the above mentioned first and second rotary filter controllers 33 and 37 and a rotary solenoid (not illustrated) driving the above mentioned movable reflecting mirrors 23 and 24 so that either may be selected by the operating panel 47.

A communication circuit 55 connected with the system controller 49 is provided within the above mentioned video processor so that, through this communication circuit 55, the video processor 5 may be connected with an endoscope filing system, photographed picture image data may be delivered, picture image data or the like may sought and taken in from the filing system and may be displayed in the first color monitor 46 and the chromaticity of the inspected part may be calculated for the picture image.

The above mentioned video process circuit 42 is connected with a spectral characteristic calculating section 56 through a measuring terminal 45.

An air feeding pump 57 is provided within the video processor 5 so as to be able to feed air to the electronic scope 2.

Figure 7:
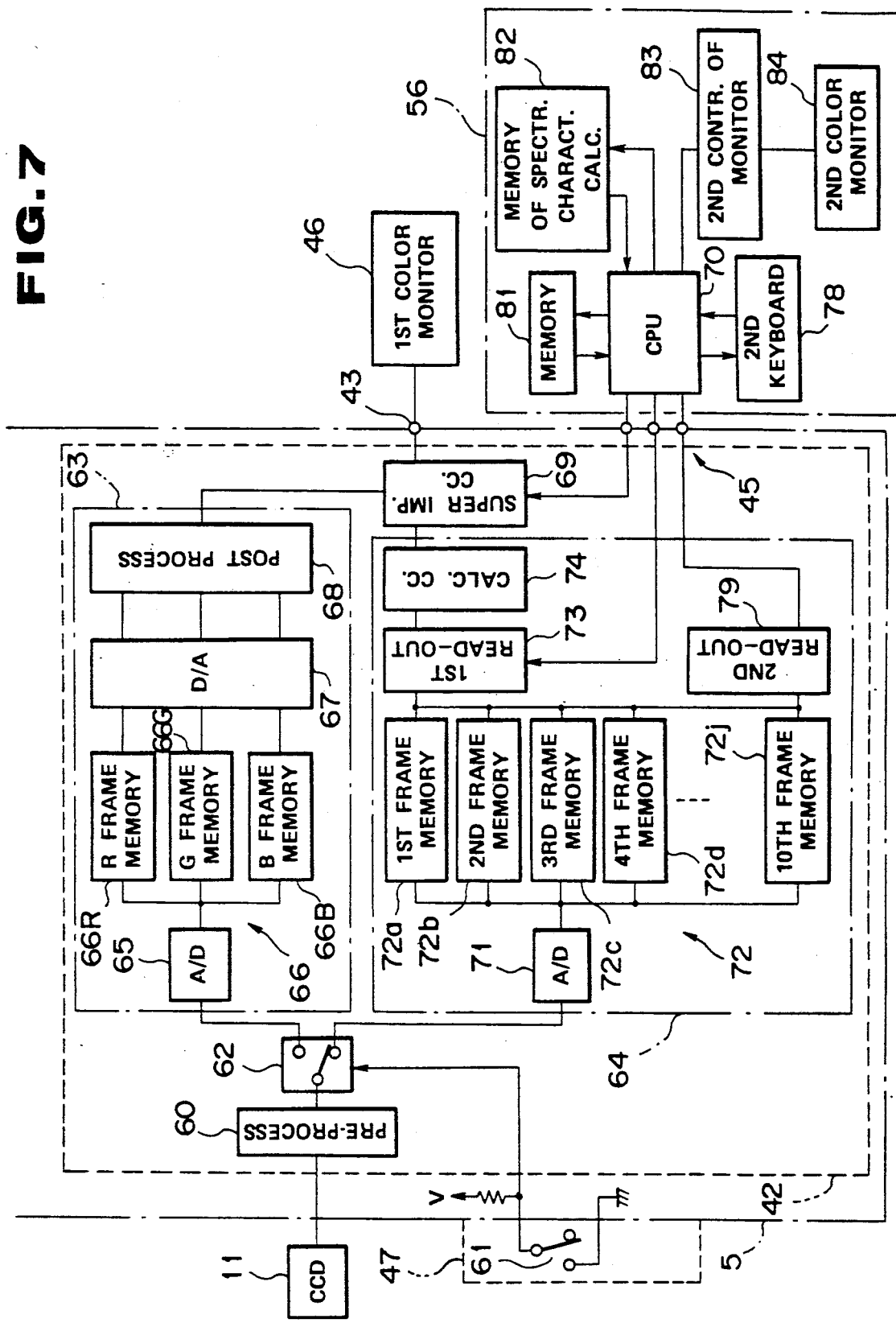

The above mentioned video process circuit 42 is of the formation shown in FIG. 7.

The output signal of the CCD 11 is input into a preprocess circuit 60, is processed to remove resetting noises and is then input into an ordinary process circuit 63 or spectral process circuit 64 by a switch 62 switched as operatively connected with a rotary filter selecting button 61 on the board of the operating panel 47.

In the above mentioned ordinary process circuit 63, by an A/D converter, an analogue signal is converted into a digital signal and is written into a memory section 66. This memory section 66 consists of R, G and B frame memories 66R, 66G and 66B. Picture image data for 1 frame imaged, for example, under a red illuminating light is written into the R frame memory 66R. When 1 frame part is written into each of the frame memories 66R, 66G and 66B, that is, 3 frame parts are written into all of the frame memories, these will be simultaneously read out, will be converted to analogue signals by a D/A converter 67, will be then input into a post-process circuit 68, will be processed to enhance the outline or the like and then will be input into a superimposing circuit 69. The signal data from a CPU 70 forming the spectral characteristic calculating section 56 are also input into this superimposing circuit 69, are superimposed on the output signal from the post-process circuit 68 and are output to the RGB output terminal 44 or NTSC output terminal 43.

In the spectral process circuit 64, the signal data are converted to digital signal data by the A/D converter 71 and are then input into a memory section 72. This memory section 72 is formed of a first, second, third, ... and tenth frame memories 72a, 72b, ... and 72j each housing 1 frame part of the picture image data photographed under the illuminating light of respective narrow band wavelengths passed through the narrow band filters 35a, 35b, ... and 35j. When 10 frame parts are written into these frame memories 72a, 72b, and 72j, they will have only an address designated in a first reading circuit 73 read out, will be input into a calculating circuit 74 and will be operated to calculate the spectral distribution. The output of this calculating circuit 74 is input into the superimposing circuit 69 and is superimposed with the video signal output from the above mentioned post-process circuit 68 and spectral distribution characteristics 77 for the position designated by a pointer 76 on an endoscope picture image 75 are displayed together with the endoscope picture image 75 as shown, for example, in FIG. 8 on the picture surface of the first color monitor 46.

Figure 8:
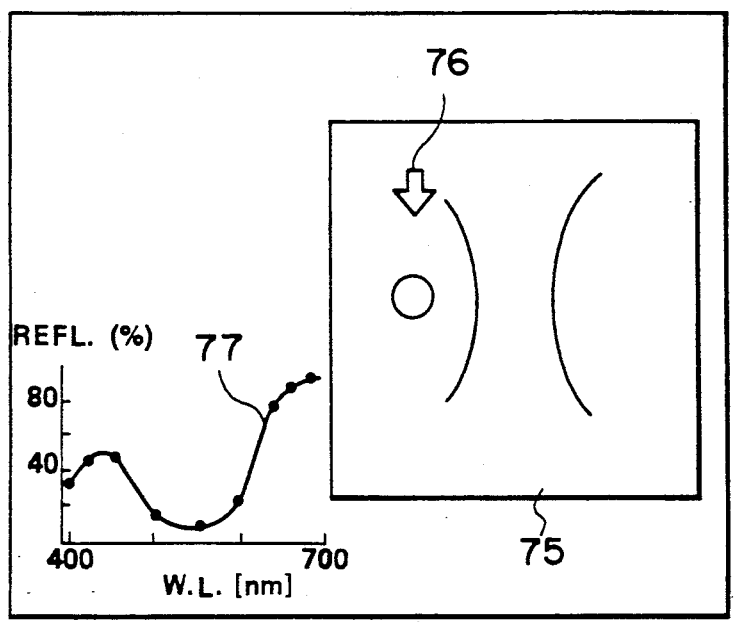

In the above mentioned first reading circuit 73, the reading address corresponding to the position of the pointer 76 shown in FIG. 8 is designated by a second keyboard connected with the CPU 70. The reading address can be designated also by the first keyboard 51.

All picture image data of the above mentioned memory section 72 are transmitted to the CPU 70 forming the spectral characteristic calculating section 56 through the measuring terminal 45 sequentially by the second reading circuit 79 and are written in the form designated by the second keyboard 78 into a large capacity memory 81 connected with this CPU 70. The data of this large capacity memory 81 are read out at any time. Such operations as the spectral characteristic calculation and chromaticity point calculation are processed by the designation of the second keyboard 78 in the CPU 70 and the results are stored in a spectral characteristic result memory 82.

The data of the above mentioned spectral characteristic result memory 82 are output by the CPU 70 and are displayed on the picture surface of a second color monitor 84.

The above mentioned calculating circuit 74 is to calculate for the inspected part a presumed spectral distribution o ($\lambda$) represented by $$p(\lambda) = \sum_{i=1}^{10} \alpha i \chi i Ci(\lambda) \quad (1)$$

where $\alpha i$ represents a constant when the presumed error $$\Delta = \int [p(\lambda) - \rho(\lambda)]^2 d\lambda \quad (2)$$

is minimal and i is an additive representing a plurality of wavelength points selected to cover an object wavelength range (for example, of 400 [nm] to 700 [nm]) to determine the presumed spectral distribution $p(\lambda)$. In this embodiment, the constants $\alpha i$ of i=1, 2, ... and 10 represent to be respectively of the wavelengths using the narrow band filters 35a, 35b, ... and 35j.

$\chi x i$ represents signal outputs obtained when the respective narrow band filters 35a, 35b, ... and 35j are used and Ci($\lambda$) represents a three-dimensional spline function.

Figure 9:
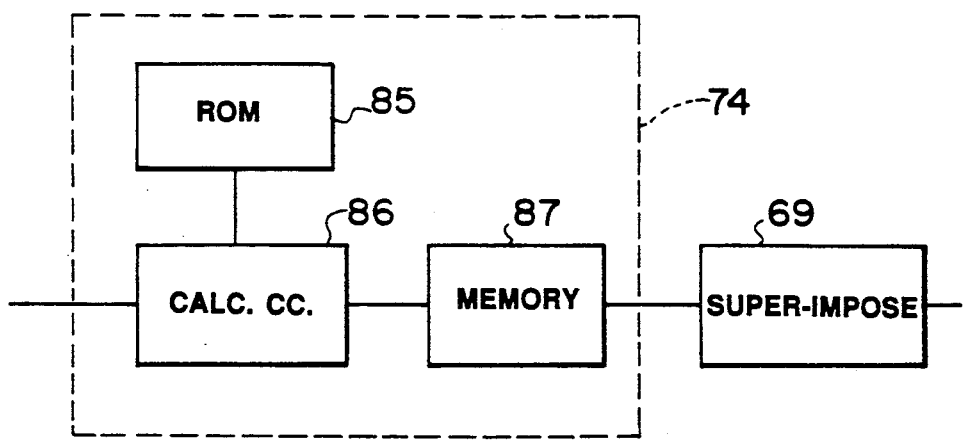
Figure 10:
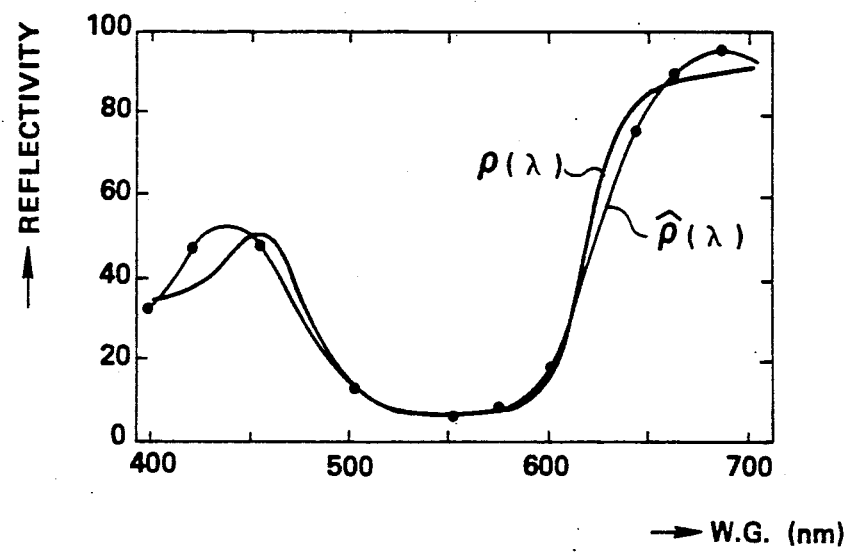

The above mentioned calculating circuit 74 is of the formation shown in FIG. 9 to determine the presumed spectral distribution $p(\lambda)$ of the formula (1).

The constant $\alpha i$ determined so that the error $\Delta$ of the formula (2) may be minimal in case an object of a known spectral distribution $\rho(\lambda)$ is imaged in advance and its presumed spectral distribution $p(\lambda)$ is to be determined according to the formula (1) is stored in a ROM 85. For the actual inspected part, the picture image data of the address designated by the pointer 76 are read out of the frame memories 72a, 72b, ... and 72j and the presumed spectral distributions $p(\lambda)$ in the respective wavelengths $\lambda$ are determined by the multiplication of the formula (1) and the total sum operating process of the multiplication results in the calculating circuit 86. Presumed spectral distribution data interpolated by the spline function Ci($\lambda$) on these presumed spectral distributions $p(\lambda)$ are housed in a memory 87, are read out by the application of a reading clock synchronized with a synchronizing signal and are transmitted to the superimposing circuit 69.

In the spectral characteristic calculating section 56, the range designated by the first or second keyboard 51 or 78 or the entire endoscope picture image is compared with the data of the normal part and affected part written in advance into the memory of the ROM or RAM and a chromaticity point is calculated and is displayed in the color monitor 84 or the like. The spectral picture image data of the respective wavelength ranges, for example, of the frame memories 72a, 72b, ... and 72j can be used as materials for determining the picture image data of which frame memories 72a, ... and 72j are high in correlation with those close to the affected part. Therefore, by displaying the picture image with the picture image data of the specific frame memory considered to be high in correlation, the possibility of the affected part can be investigated within a short time with the luminance level.

The operation of this embodiment shall be explained in the following.

Ordinarily, the first rotary filter 29 is selected by the operating panel 47. At this time, the information of the operating panel 47 will be transmitted to the system controller 49 through the controller 48. The system controller 49 rotates the movable reflecting mirrors 23 and 24 by 90 degrees with the rotary solenoids and set them as shown by the dotted lines in FIG. 3. In this state, the light of the xenon lamp 18 lit by the electric power input through the lighting circuit 19 from the lamp current source 20, is adjusted in the passed light amount by the iris 21, is then reflected by the movable reflecting mirror 23 through the lens 22 and advances along the light path on the fixed reflecting mirror 25 side. The light reflected by this fixed reflecting mirror 25 passes through the first rotary filter 29 and is input to the entrance end surface of the light guide 13 through the fixed reflecting mirror 26 and movable reflecting mirror 24.

As the above mentioned first rotary filter 29 is fitted with the color transmitting filters 32R, 32G and 32B transmitting the respective color light of red, green and blue as shown in FIG. 4, when this first rotary filter 29 is rotated by the motor 34, these light transmitting filters 32R, 32G and 32B will be sequentially interposed into the light path and the illuminating light passed through this first rotary filter 29 will become frame sequential illuminating light of red, green and blue.

The object image of the inspected part or the like illuminated under the above mentioned frame sequential illuminating light is formed on the imaging surface of the CCD 11 by the objective lens 10 and is accumulated as a signal charge.

This accumulated signal charge is read out by the application of a driving signal from the CCD driver 41 within the video processor 5 through the signal cable 12, is input into the frame sequential video process circuit 42 and is processed to be a video signal, an NTSC composite video signal is output from the NTSC output terminal 43 and R, G and B signals are output from the RGB output terminal 44. A scope picture image is displayed by the first color monitor 46 connected to one of these output terminals 43 and 44.

For a spectral measurement, the side passing through the second rotary filter 30 will be selected by the selecting button 61 of the operating panel 47. At this time, the rotary solenoid (not illustrated) will be operated by the system controller 49, the movable reflecting mirrors 23 and 24 will rotate and will be set as shown by the solid lines in FIG. 3 and the light from the xenon lamp 18 will be reflected on the second rotary filter 30 side. Using the second rotary filter 30, the illuminating light becomes frame sequential illuminating light of multichannel color light such as are shown in FIG. 6. The respective color light illuminate the inspected object through the light guide 13. The reflected light is made to form an image on the CCD 11 by the objective lens 10 and the output is photoelectrically converted. The output signal photoelectrically converted by the CCD 11 is input into the pre-process circuit 60, is processed to remove resetting noise or the like and is then converted to digital data by the A/D converter 71. The digital data is then input into the memory section 72 and is written into the frame memories 72a to 72j of the picture images corresponding to the respective color light. Of the data written into these frame memories 72a to 72j, 10 picture image data read out of the first reading circuit 73 outputting only the address designated by the first keyboard 51 or second keyboard 78 are input into the calculating circuit 74 and the spectral distribution is calculated. That is to say, the unknown presumed spectral distribution is presumed by calculating $_p(\lambda)$ of the above described formula (1) by using the output $\chi i$ obtained from the respective channels of the respective filters 35a, ... and 35j of the second rotary filter 30 and the three-dimensional spline function $Ci(\lambda)$ by using the constant $\alpha i$ determined so that the presumed error $\Delta$ represented by the formula (2) may be minimal in advance for the spectral distribution and presumed spectral distribution $_p(\lambda)$ and $_p(\lambda)$. The output of this calculating circuit 74 is superimposed as designated by the first keyboard 51 or second keyboard 78 in the superimposing circuit 69 and is displayed as shown in FIG. 8 on the first color monitor 46 through the NTSC output end 43. The precision of this presumed spectral distribution is found to be practical from measuring and comparing the known spectral reflectivity distribution $\rho(\lambda)$ and the presumed spectral distribution $_p(\lambda)$ determined in the present invention with each other.

All the picture image data of all the frame memories 72a to 72j read out by the second reading circuit 79 are written into the large capacity memory 81 through the CPU 70 by the form designated by the second keyboard 78 through the measuring terminal 45. The data is read out at any time by the second keyboard 78, the presumed spectral distributions $_p(\lambda)$ of all the pixels are presumed by the above described spectral distribution presuming method and thereby the chromaticity point or the like is calculated and is recorded in the spectral characteristic calculation result memory 82. The data is read out in the CPU 70 by the second keyboard 78 and is extracted on the second color monitor 84 through the second monitor controller 83.

Figure 11:
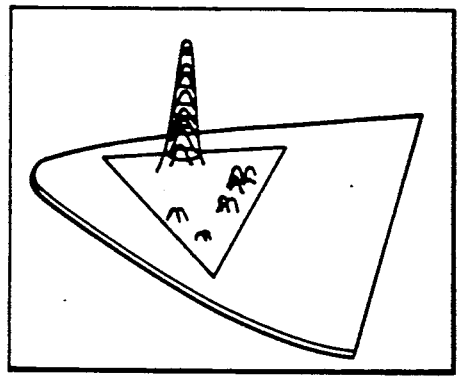

The chromaticity points of all the pixels are represented by the histogram on the chromaticity diagram and are displayed as in FIG. 11 wherein the triangular part represents the chromaticity range of the CRT and the color outside the triangle is represented as the color on the shortest side of the triangle.

Figure 12:
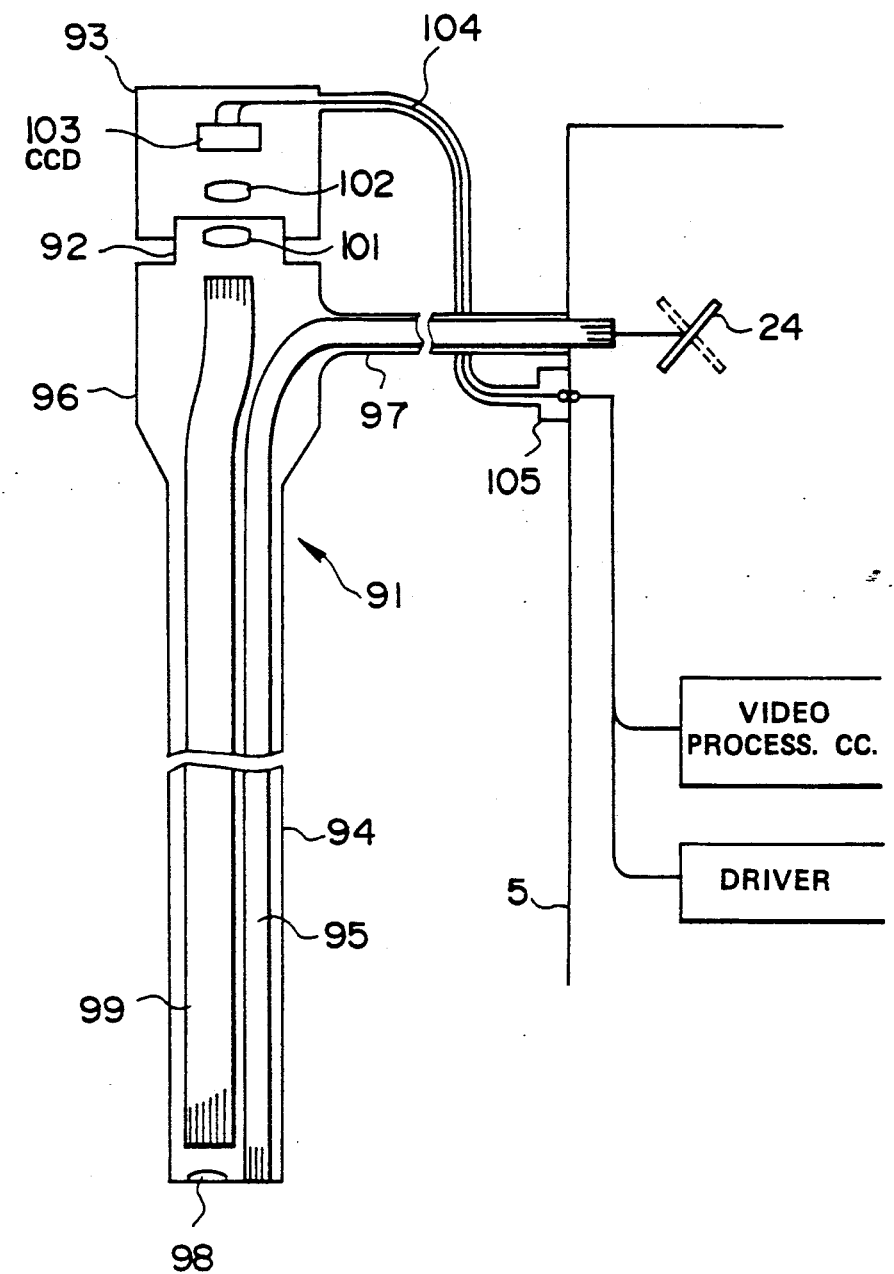
FIG. 12 is a formation view showing a fiber scope and a television camera connected to this fiber scope in the second embodiment of the present invention.

As the spectral distribution has high precision as in the above can be determined, diagnosis by the chromaticity point as is described in the above described Japanese Patent Application No. 260015/1987 is possible objectively within a short time and a powerful auxiliary means of diagnosing affected parts can be provided FIG. 12 shows essential parts of the second embodiment of the present invention.

In this embodiment, a fiber scope 91 and a television camera 93 fitted to the eyepiece section 92 of this fiber scope 91 are used instead of the electronic scope 2.

In the above mentioned fiber scope 91, a light guide 95 is inserted through an elongate insertable section 94, is further inserted through a light guide cable 97 extended out of an operating section 96 and is connected at the entrance end with a light source connector receptacle of a video processor 5 so that an illuminating light may be input in the same manner as in the first embodiment.

An objective lens 98 is fitted to the tip portion of the above mentioned insertable section 94 so as to form an optical image in the focal plane. The entrance end surface of the image guide 99 is present in this focal plane so as to transmit the optical image to the exit end surface within the operating section 96 or eyepiece section 92. An eyepiece lens 101 is arranged opposed to this exit end surface so that a naked eye observation may be possible through this eyepiece lens 101 and the television camera 93 may be fitted to the eyepiece section 92. This television camera 93 is provided with an image forming lens 102 opposed to the eyepiece lens 101 so that an image at the exit end of the image guide may be formed on a CCD 103 through the eyepiece lens 101 and image forming lens 102. A signal connector 105 provided on a signal cable 104 can be connected to a signal connector receptacle of the video processor 5 through this cable 104 so that a driving signal may be applied to the CCD 103 and a photoelectrically converted signal may be output to a video process circuit 42.

The other parts are the same as in the above mentioned first embodiment.

In the above described respective embodiments, the spectral measuring filters are not limited to be 10.

As described above, according to the first and second embodiments, since the endoscope provided with an imaging means is provided with a sequential illuminating means sequentially illuminating an object through a multichannel spectral filter and a spectral distribution presuming means presuming the spectral distributions of the respective parts of the object by processing the output signal of an imaging signal, spectral data in the two-dimensional directions so high in precision and objective as to be a powerful auxiliary means of diagnosing affected parts can be easily obtained.

The third embodiment of the present invention shall be explained in the following with reference to FIGS. 13 to 19.

The endoscope apparatus of the third embodiment is provided with an electronic endoscope 141 as shown in FIG. 14. This electronic endoscope 141 has an elongate and for example, flexible insertable section 142 and a thick operating section 143 connected to this insertable section at the rear end. A flexible universal cord 144 is extended sidewise out of the rear end part of this operating section 143 and is provided at the tip with a connector 145. The above mentioned electronic endoscope 141 is to be connected to a video processor 146 having a light source apparatus and a signal processing circuit built in. This video processor 146 is to be connected with an observing monitor 147 and various signal processing apparatus not illustrated.

The above mentioned insertable section 142 is provided on the tip side with a rigid tip section 149 which is provided adjacently on the rear side with a curvable section 150. The above mentioned operating section 143 is provided with a curving operation knob 151 so that the above mentioned curvable section 150 may be curved vertically and horizontally by rotating this curving operation knob 151. The above mentioned operating section 143 is provided with an inserting port 152 communicating with a treating instrument channel provided with the above mentioned insertable section 142.

Figure 13:
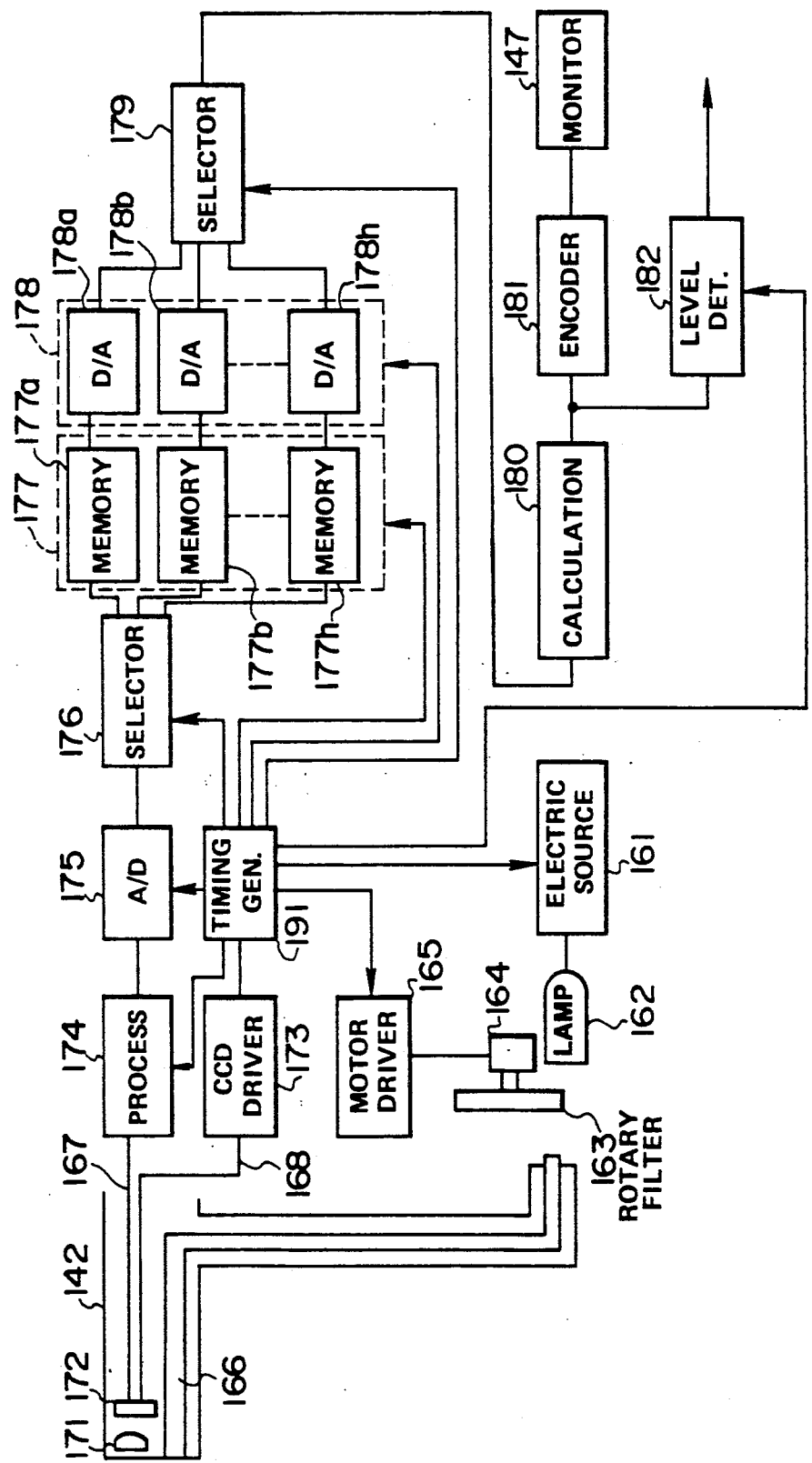

As shown in FIG. 13, a light guide 166 transmitting an illuminating light is inserted through the insertable section 142 of the electronic endoscope 141 and is arranged on the tip surface in the tip section 149 of the above mentioned insertable section 142 so that an illuminating light may be emitted from this tip section. The above mentioned light guide 166 is inserted on the entrance end side through the above mentioned universal cord 144 and is connected to the above mentioned connector 145. By connecting this connector 145 to the above mentioned observing apparatus 146, the illuminating light emitted from the light source apparatus within this observing apparatus 146 may be incident upon the entrance end surface of the above mentioned light guide 166. Also, the tip section 149 is provided with an objective lens system 171. A solid state imaging device as, for example, a CCD 172 is arranged in the image forming position of this objective lens system 171. Signal lines 167 and 168 are connected to this CCD 172, are inserted through the above mentioned insertable section 142 and universal cord 144 and are connected to the above mentioned connector 145.

The video processor 146 is provided with a light source section as a light feeding means having a lamp 162 emitting light in a wide band from ultraviolet rays to infrared rays, a current source 161 inputting an electric current to this lamp 162 and, as arranged in the illuminating light path of the above mentioned lamp 162, a rotary filter 163 time sequentially color-separating the light emitted from the above mentioned lamp 162, a motor 164 rotating and driving this rotary filter 163 and a motor driver 165 controlling this motor 164.

As shown in FIG. 15, the above mentioned rotary filter is provided in the peripheral direction with a plurality of color-separating filters 163a, 163b, 163c, 163d, 163e, 163f, 163g and 163h which have respectively characteristics of transmitting the light of the wavelength ranges of a, b, c, d, e, f, g and h shown in FIG. 16.

The light emitted from the above mentioned lamp 161 is time sequentially separated into the above mentioned respective wavelength ranges of a, b, . . . and h by the above mentioned rotary filter 163, is incident upon the entrance end of the above mentioned light guide 166, is led to the tip section 149 by the above mentioned light guide 166 and is emitted from this tip section 149 to radiate an object.

The CCD 172 is arranged in the image forming position of the above mentioned objective lens system 171. The object image illuminated by the above mentioned frame sequential illuminating light is formed by the above mentioned objective lens system 171 and is converted to an electric signal by the above mentioned CCD 172. The picture image signal from this CCD 172 is read out at a high speed by the application a driving signal from a CCD driver 173, is input into a process circuit 174 and is processed to be converted into a video signal. This video signal is then input into an A/D converter 175 to be converted to a digital signal, is further input into a selector circuit 176 and is branched into respective wavelength ranges. The branched video signals are stored respectively in memories 177a, 177b, . . . and 177h within a memory section 177 as a memorizing means. The respective video signals stored in this memory section 177 are then input into a D/A converting section 178 and are respectively converted into analogue signals by respective D/A converters 178a, 178b, . . . and 178h within this D/A converting section 178. These analogue-converted respective video signals are selected by a selecting circuit 179 as a selecting means, are then calculated and processed by the calculating process circuit 180 and are then converted to signals displayable as video signals by an encoder circuit 181 so that the picture image may be displayed in the monitor 147.

This endoscope apparatus 142 is further provided with a level detecting circuit 182 for detecting the levels of the video signals calculated and processed by the above mentioned calculating process circuit 180 and making them numerical data.

The above mentioned calculating process circuit 180, encoder 181 and level detecting circuit 182 form a calculating means.

Also, a timing generator 191 is provided to control the timing of the operation of the above mentioned respective circuits and is connected to the above mentioned motor driver 165, CCD driver 173, process circuit 174, A/D converter 175, selector circuit 176, the respective memories of the above mentioned memory section the respective D/A converters of the above mentioned D/A converting section 178, the above mentioned selecting circuit 179 and level detecting circuit 182 for which synchronizing signals are to be generated.

The operation of this embodiment formed as in the above shall be described in the following.

A motor driving signal is transmitted from the motor driver 165 to the motor 164 rotating and driving the rotary filter 163. The above mentioned motor 164 rotates the above mentioned rotary filter 163 by this driving signal The illuminating light emitted from the lamp 162 is time sequentially separated into light of the respective wavelength ranges of a, b, c, d, e, f, g and h shown in FIG. 16 by passing through the above mentioned rotary filter 163 and is incident upon the entrance end of the light guide 166 of the electronic endoscope 141. This illuminating light is led to the tip section 149 by the above mentioned light guide 166, is emitted from the tip surface and is radiated to an object.

The object image illuminated by the light of the above mentioned respective wavelength ranges is formed on the CCD 172 by the objective lens system 171 and is converted to an electric picture image signal by this CCD. This picture image signal is read out by the application of a driving signal from the CCD driver 173, is converted to a video signal by the process circuit 174, is then converted into a digital signal by the A/D converter 175, is further input into the selector circuit 176 and is stored for the respective corresponding wavelength ranges respectively in the respective memories 177a, 177b, . . . and 177h as video signals separated sequentially into narrow bands of wavelengths from this selecter circuit 176. The picture image signals stored in these respective memories 177a, 177b . . . and 177h are synchronized and read out, are converted to analogue type picture images by the respective D/A converters of the D/A converting section 178, are then selected by the selecting processing means 179 and are input into the calculating process circuit 180.

Figure 17:
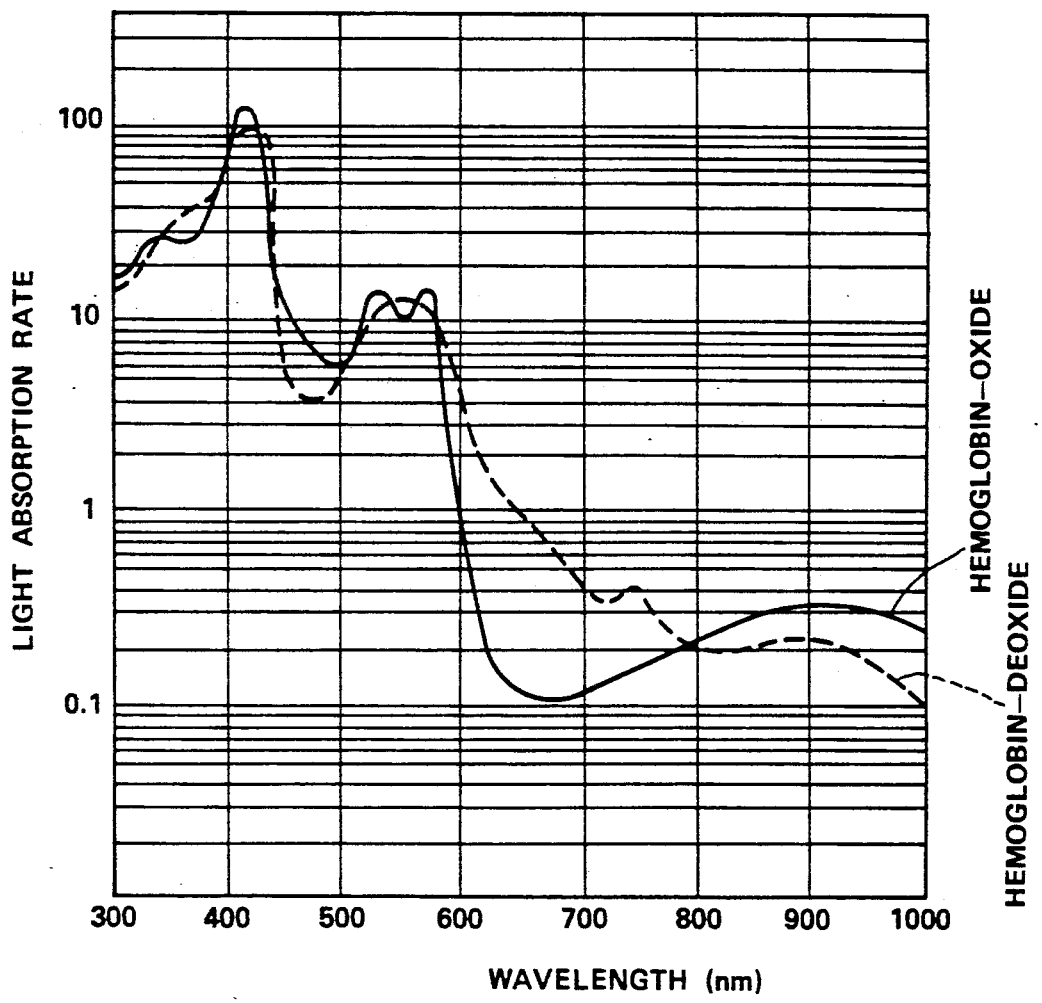

Spectral characteristics of hemoglobin are shown in FIG. 17. As clear from this diagram, when the hemoglobin oxygen saturation degree ($SO_2$) varies, the spectral characteristics of the blood will vary with it. In this FIG. 17, the spectral characteristics of hemoglobin oxide and hemoglobin deoxide are shown to indicate the variation of the light absorption rate with the variation of $SO_2$. Hence it is found that, in the regions of wavelengths near 580 nm and near 800 nm, even if $SO_2$ varies, the light absorption rate of the blood will not substantially vary. It is also found that, in the region of wavelengths near 650 nm, the light absorption rate of the blood will vary with the variation of $SO_2$. Therefore, the variation of $SO_2$, can be determined by its difference signal, division signal or the like from the picture images by these three wavelength regions. On the other hand, the distribution amount and two-dimensional data of hemoglobin can be obtained by detecting the picture image signals of wavelengths of 600 to 800 nm in which the light absorption rate of the blood varies greatly and processing them by the above mentioned calculating process circuit 180.

Figure 18:
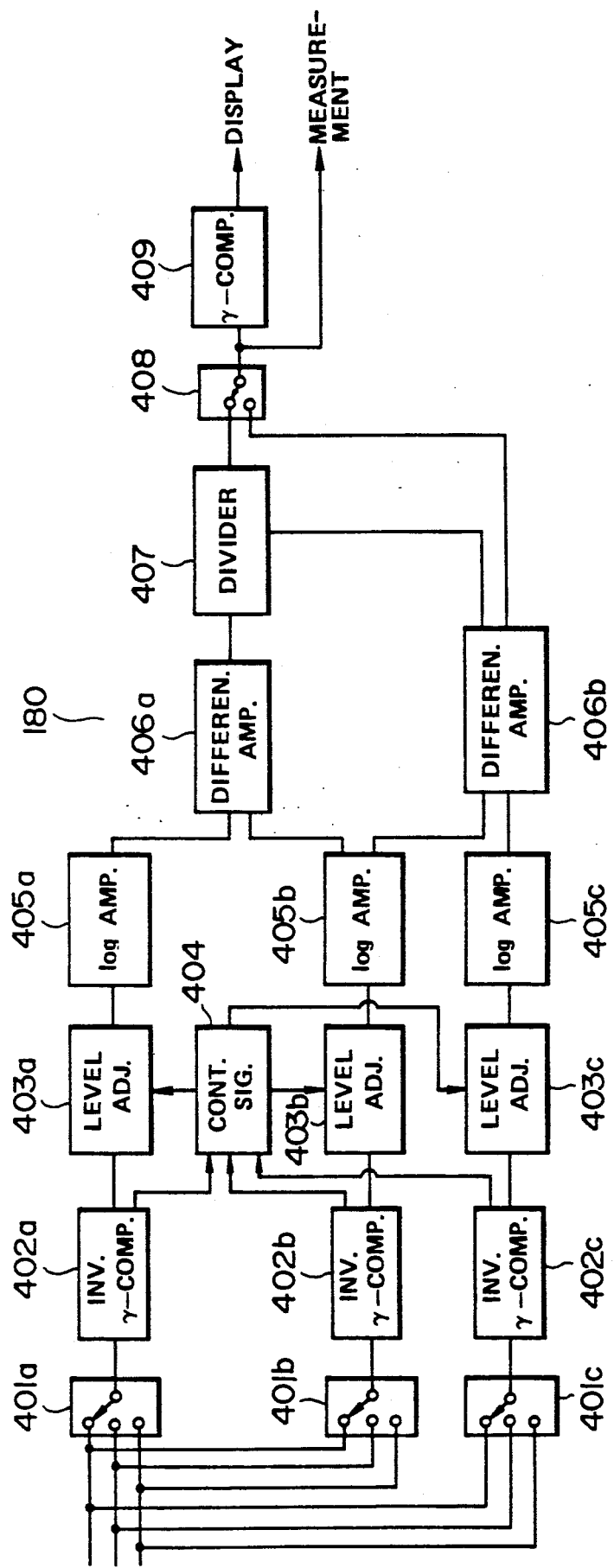

The circuit formation of the above mentioned calculating process circuit 180 is shown in FIG. 18. As shown in this diagram, the above mentioned calculating process circuit 180 has three 3-input 1-output selectors 401a, 401b and 401c. The picture image signals corresponding to the respective wavelengths are to be input respectively into the inputs of these respective selectors 401a, 401b and 401c. The above mentioned respective selectors 401a, 401b and 401c are to select and output the picture image signals corresponding to the wavelengths different from each other. The outputs of the above mentioned respective selectors 401a, 401b and 401c are input respectively into inverse γ—compensating circuits 402a, 402b and 402c so as to be inverse γ—compensated to return the γ compensation already made in the above mentioned video processor 146. The outputs of the above mentioned inverse γ—compensating circuits 402a, 402b and 402c are input respectively into level regulating circuits 403a, 403b and 403c which are to regulate the levels, for example, by varying the gains by level regulation controlling signals output from a level regulation controlling signal generating circuit 404 so that the entire levels may be thereby regulated. Further, as the ordinate in the graph showing the variation of the light absorption rate of the blood with the variation of the oxygen saturation degree as shown, for example, in FIG. 17 is a logarithmic ordinate, the outputs of the above mentioned level regulating circuits 403a, 403b and 403c are logarithmically converted respectively by logarithmic amplifiers 405a, 405b and 405c.

The outputs of the two logarithmic amplifiers 405a and 405b of these three logarithmic amplifiers 405a, 405b and 405c are input into a differential amplifier 406a so that the difference between the picture image signals corresponding to two wavelengths may be calculated. In the same manner, the outputs of the two log amplifiers 405b and 405c are input into a differential amplifier 406b so that the difference between the picture image signals corresponding to two wavelengths of another combination may be calculated.

In case the outputs from the color transmitting filters 163e, 163g and 163h among the respective outputs of the above mentioned D/A converting section 178 are selected by a switching circuit 179, the difference between the picture image signal corresponding to the region in which the light absorption rate of the blood does not substantially vary with the variation of $SO_2$ and the picture image signal corresponding to the region in which the light absorption rate of the blood varies with the variation of $SO_2$ will be calculated and how much of oxygen is dissolved in the inspected object, that is, the oxygen saturation degree will be able to be known from this difference.

When the outputs of the above mentioned differential amplifiers 406a and 406b are used to determine the oxygen saturation degree $SO_2$ are input into a divider 407 and are calculated as predetermined by this divider 407 and the outputs by the above mentioned color transmitting filters 163e, 163g and 163h are selected, the above mentioned $SO_2$ will be determined. The output of the above mentioned differential amplifier 406b will be used to observe and measure the variations of the flow volume of the blood, the running state of the vein and the hemoglobin amount in case the respective outputs from the above mentioned color transmitting filters 163e and 163h or the respective outputs from the above mentioned color transmitting filters 163e and 163f are selected and even in the case of either combination. The output of the above mentioned divider 407 and the output of the above mentioned differential amplifier 406b are input into a selector 408 of two outputs and one of the signal showing $SO_2$ and the signal showing the variations of the blood flow volume, vein running state and hemoglobin amount is selectively output.

In case the output signal of the above mentioned selector 408 is to be used for the measurement, it will be taken out as it is, will be made numerical data by the level detecting circuit 182 and will be output. On the other hand, in case it is to be used for the display, it will be γ—compensated again by the γ—compensating circuit 409, will then be encoded by the encode 181 and will be output as a picture image in the above mentioned monitor 147.

In the calculating process circuit 180 shown in FIG. 18, the calculation is made by hardware but may be made by software.

Figure 19:
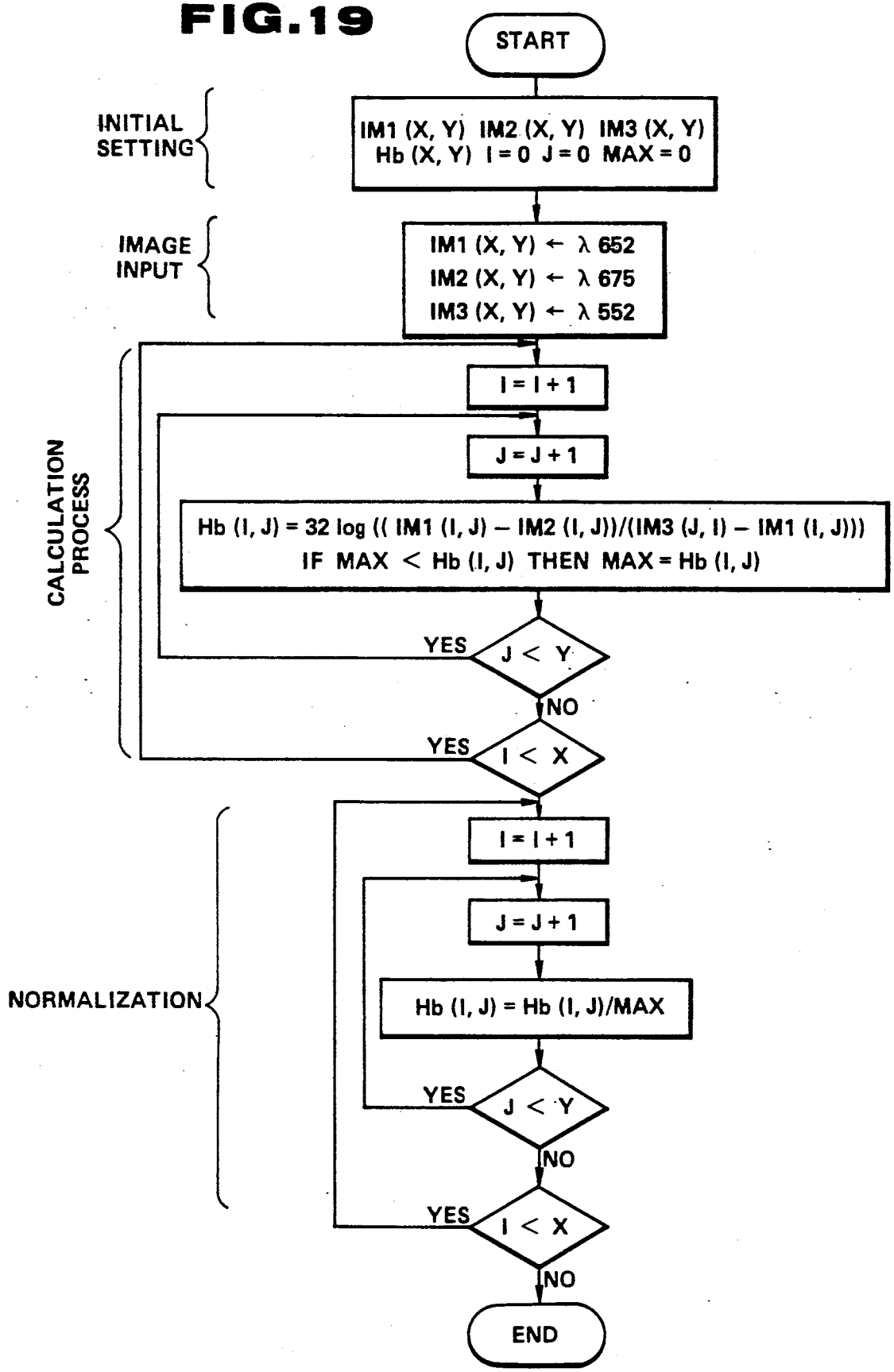

A flow chart of the calculation to determine the hemoglobin amount is shown in FIG. 19. If a picture image is represented by a two-dimensional array IM(X,Y), X will signify the size of the picture image in the X direction and Y will signify the size of the picture image in the Y direction. If a hemoglobin image is represented by Hb(X,Y), X and Y will signify the sizes of the hemoglobin image respectively in the X direction and Y direction. A picture image corresponding to a wavelength A is represented by $\lambda_A$.

First of all, as an initial setting, a variable I showing the position in the X direction, variable J showing the position int he Y direction and variable MAX showing the maximum value are initiated (replaced with 0).

As picture image inputs, three picture images IM1(X,Y), IM2(X,Y) and IM3(X,Y) to be processed are replaced respectively with a picture image $\lambda_{652}$ at a wavelength of 652 nm, picture image $\lambda_{675}$ at a wavelength of 675 nm and picture image $\lambda_{552}$ at a wavelength of 552 nm.

As a calculating process, the maximum value of hemoglobin is processed to be determined. This calculating process is made by the steps shown in the following:
(1) I is 1-counted up.
(2) J is 1-counted up.
(3) The hemoglobin image Hb(I,J) is replaced with a multiplication of the logarithmic ratio of the difference between IM1(I,J) and IM2(I,J) and the difference between IM3(I,J) and IM1(I,J) by 32. In case the value of this hemoglobin image Hb(I,J) is larger than MAX, MAX=Hb(I,J).
(4) If J<Y, the process will return to (2) or, if not so, the process will move to (5).
(5) If I<X, the process will return to (1) or, if not so, the process will move to the next normalizing step.

By the above steps, the maximum value of the hemoglobin is determined.

Then, a normalization is made. This normalization is made by the respective steps shown in the following:
(1) I is 1-counted up.
(2) J is 1-counted up.
(3) Hb(I,J) showing the hemoglobin image is made Hb(I,J)=Hb(I.J)/MAX.
(4) If J<Y, the process will return to (2) or, if not so, the process will move to (5).
(5) If I<X, the process will return to (1) or, if not so, the process will end.

By the above steps, the maximum value of the hemoglobin determined by the calculating process step is normalized and the amount of the hemoglobin is determined.

As described above, according to this embodiment, some of a plurality of color signals by the illuminating light divided into a plurality of bands are combined, are selectively read out and are processed to obtain a picture image effective to diagnose a deep vein image or hemoglobin distribution image. Also, spectral characteristics of living body tissues are determined, the chromatic data can be output as numerical values and can be displayed as picture images. Thus, auxiliary information for objective judgement in a diagnosis can be obtained.

In this embodiment, respective signals from respective color transmitting filters are selected and read out. However, the rotary filter 163 may be provided with only the color transmitting filters 163e, 163g and 163 h but may not be provided with the selecting circuit 179 so that only $SO_2$ may be output in the formation.

Figure 20:
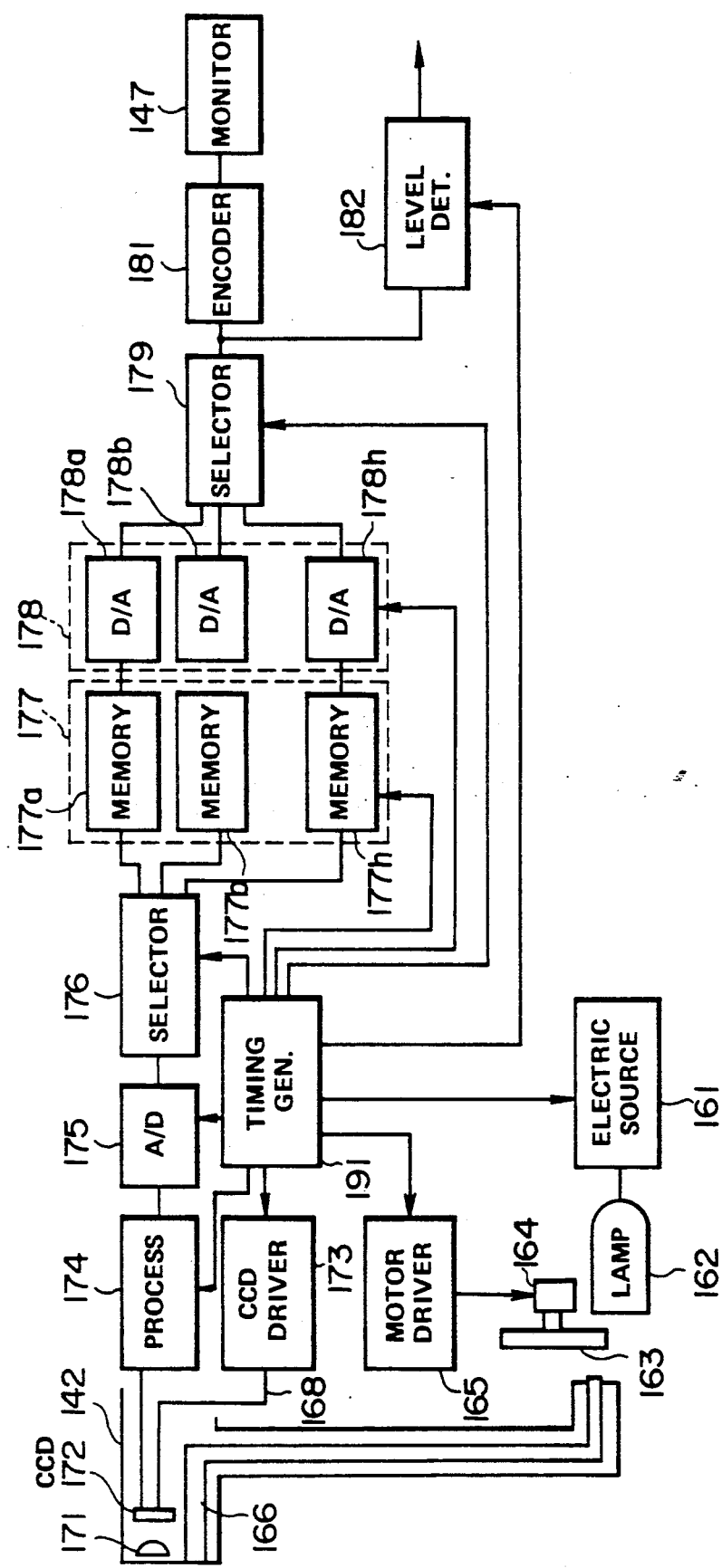

FIG. 20 shows the formation of the fourth embodiment of the present invention. In this fourth embodiment, the calculating process circuit 180 of the above mentioned third embodiment is not provided and the video signal selected by the selecting means 179 is made a video image without being processed to be calculated.

This fourth embodiment is the same as the above mentioned third embodiment except that the above mentioned calculating process circuit 180 is not provided.

Figure 21A:
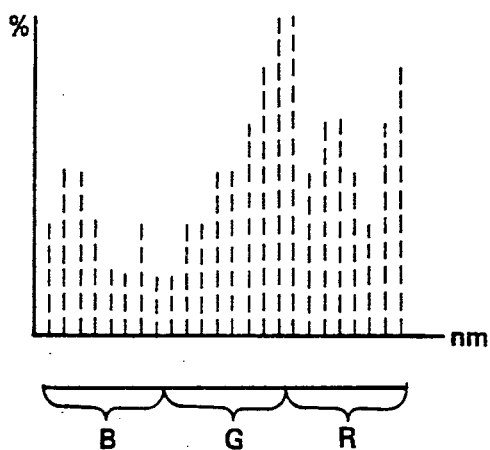
FIG. 21A-21D show diagrams showing color reproducible ranges in case the bands of R, G and B signals are narrowed.
Figure 21B:
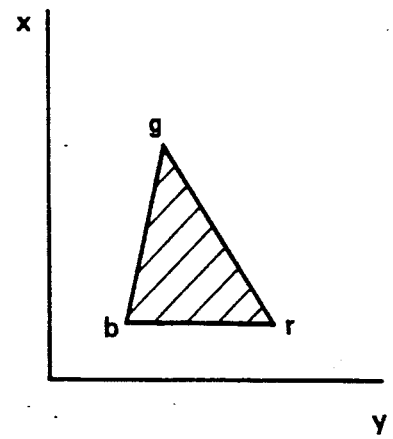
Figure 21C:
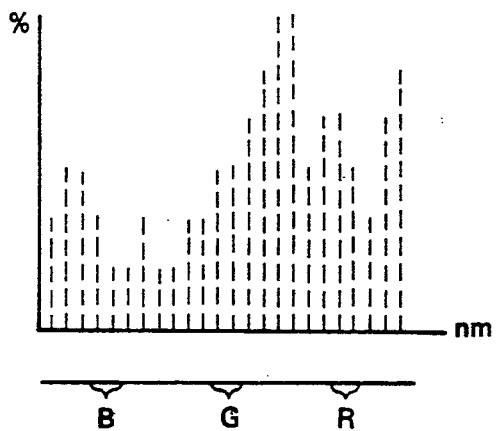
Figure 21D:
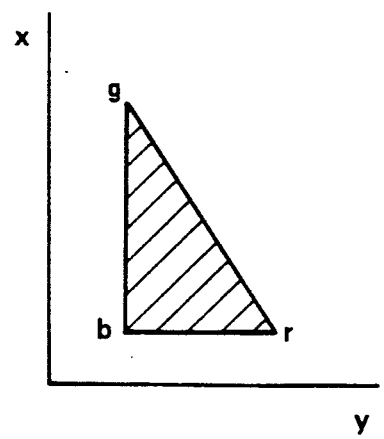

From among the respective picture image signals spectralized to be signals over a wide band from the ultraviolet range to the infrared range, respective combinations of the signal from the color transmitting filter 163b and the signal from the color transmitting filter 163c, of the signal from the color transmitting filter 163d and the signal from the color transmitting filter 163e and of the signal from the color transmitting filter 163f and the signal from the color transmitting filter 163g are selected and read out by the selecting means 179, the same RGB video signals as by the ordinary, that is, conventional endoscope apparatus will be obtained. As shown in FIG. 21A, such RGB video signals are formed by three-dividing the entire visible range on the spectral reflection characteristics of the living body tissue to be an object. The color reproduction range which can be reproduced in this case is shown in FIG. 21B. In the case of thus forming a video signal, that is, in the case of the conventional endoscope, the video signal is formed by using all the bands and therefore it is difficult to elevate the chromaticity of three primary colors RGB. Therefore, when the signal from the color transmitting filter 163b, the signal from the color transmitting filter 163c and the signal from the color transmitting filter 163f are selected from among the above mentioned respective picture image signals so as to be signals of B, G and R, the respective bands of RGB will be narrowed and thereby, as shown in FIG. 21D, the chromaticity of the three primary colors RGB will be able to be elevated and the color reproducing range which can be handled will be able to be expanded. In case a video signal is thus formed, it will be different from the ordinary video signal and therefore the reproduced Picture image will not be of perfect natural colors but will be useful to handle a delicate color variation of an affected part or the like.

Figure 22:
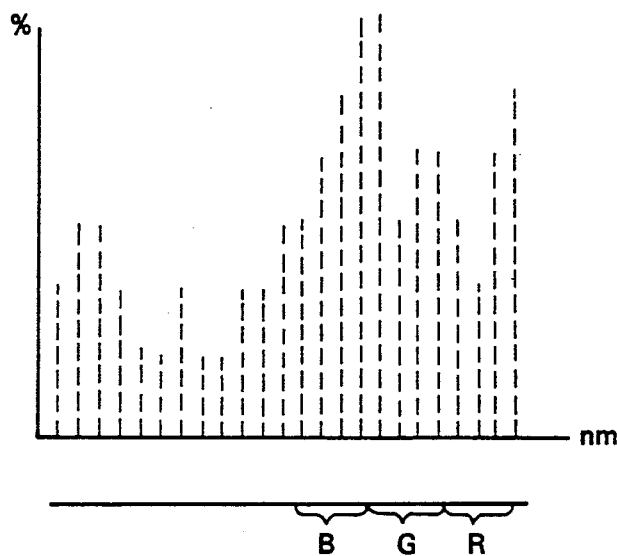

Also, as shown in FIG. 22, when the RGB signals are shifted to the red range in which the colors most concentrate on the living body tissue and a picture image is formed of only the video signals from the respective color transmitting filters in the red range, the delicate variation of the red color will be able to be displayed as a quasi-color. Further, even in case such dyeing as of methyl blue is made, when the RGB signals are shifted to the tone range of the dyeing liquid, the boundary of the dyed part will be able to be displayed as of a quasi-color and the discrimination will be thereby made easy.

As described above, in this fourth embodiment, as the bands of the RGB signals can be freely selected, the ordinary RGB video signals can be obtained and, by narrowing the bands of the RGB signals, the color reproducing range which can be handled can be expanded and the delicate color variation of the affected part or the like can be caught. Further, when the RGB signals are shifted to be concentrated in one color range, the delicate variation on this color will be able to be observed.

Figure 23A:
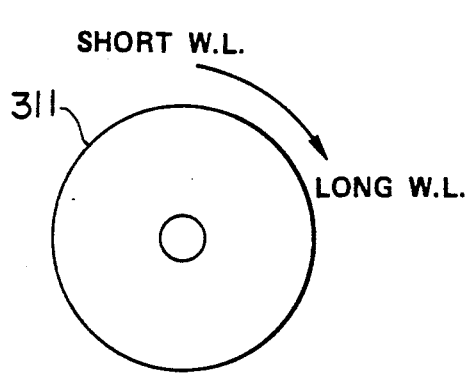
FIGS. 23(A)-23(B) are diagrams showing a rotary filter and the relation of the transmitted wavelength with the rotation angle of the rotary filter.
Figure 23B:
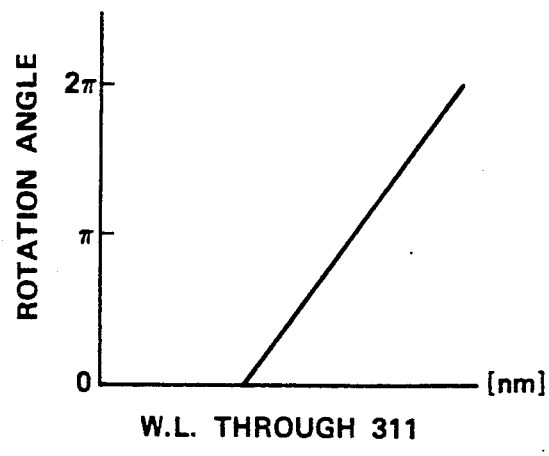
Figure 25:
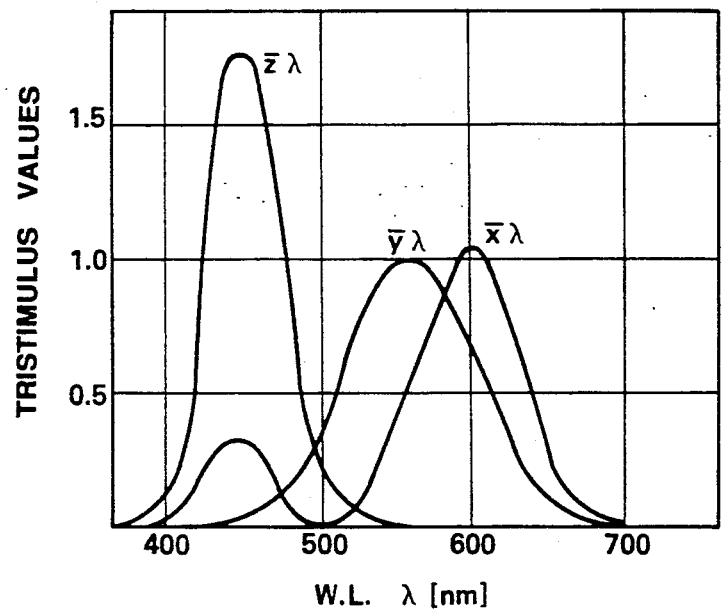

FIG. 23 shows a rotary filter in the fifth embodiment of the present invention. The rotary filter 311 shown here is a linear interference filter which is not of the formation wherein the band pass filter is incorporated into a plurality of kinds of frames as in the rotary filter 163 in the above mentioned third embodiment but is of the formation wherein the transmitted wavelengths continuously vary with the position on the periphery. In this rotary filter 311, as the number of divisions of the wavelengths is larger than in the rotary filter 163 of the above mentioned third embodiment, the respective memories and D/A converters forming respectively the memory part 177 and D/A converting part 178 are provided in the numbers as required therefor.

The other formations of the endoscope apparatus of this fifth embodiment are the same as in the above mentioned third embodiment. The same elements are explained by attaching the same reference numerals. The operation common with that of the third embodiment is not explained here.

In this fifth embodiment, the illuminating light from the lamp 161 is continuously spectralized by the linear interference filter 311. The picture image signal obtained by this spectralized illuminating light is read out at a predetermined timing under the control of the timing generator 191 and the picture image signals of any wavelength ranges are stored in the respective memories of the memory section 177. Then, the signals stored, in the above mentioned respective memories are read out by the selecting means through the respective D/A converters of the D/A converting section 178 and are processed by the calculating process circuit 180 according to the flow chart shown in FIG. 24 to calculate the chromaticity coordinates at the respective points of the observed image.

Before describing the respective steps in the flow chart in FIG. 24, the color displaying system of CIE (International Illumination Committee) and the formula showing the L*a*b* chromaticity space shall be explained.

If the spectral composition is represented by $\psi(\lambda)$, its color stimulation will be represented by the following three stimulating values X, Y and Z.

$$P = A \Sigma \psi(\lambda) \times p$$

(P:X,Y,Z:
p:x(K), y(K), z(K)).

Here, if the spectral composition of the observing light source is represented by $P_O(K)$ and the spectral reflectivity of the object is represented by IM(I, J, K), $$\psi(\lambda) = P_O(K) \, IM(I, J, K).$$

Therefore, $$X = A \Sigma IM(I, J, K) \times P_o(K) \times x(K) \quad \text{(First formula)}$$

$$Y = A \Sigma IM(I, J, K) \times P_o(K) \times y(K) \quad \text{(Second formula)}$$

-continued $$Z = A \Sigma IM(I, J, K) \times P_o(K) \times z(K). \quad \text{(Third formula)}$$

In case the stimulating value Y is proportional to the measured light amount and $\psi(\lambda)$ is given by [W/nm], the constant A will be k=683 [1 m/W].

If the three stimulating values are normalized and represented by the value of Y when IM(I, J, K) = 1, $$A = 100/P_O(K)y(K) \quad \text{(Fourth formula)}$$

and the value of Y in this case is the sight reflectivity (transmittivity).

Also, the L*a*b* chromaticity space of CIE is given by the following respective formulae:

$$LAB(I, J, 1) = 116(Y/Y_o)^{\frac{1}{3}} - 16. \quad \text{(Fifth formula)}$$
$$LAB(I, J, 2) = 500[(X/X_o)^{\frac{1}{3}} - (Y/Y_o)^{\frac{1}{3}}]. \quad \text{(Sixth formula)}$$
$$LAB(I, J, 3) = 200[(Y/Y_o)^{\frac{1}{3}} - (Z/Z_o)^{\frac{1}{3}}]. \quad \text{(Seventh formula)}$$

Now, respective steps in the flow chart shall be explained.

First of all, as the initial setting. IM(X, Y, 41), LAB(X, Y, 3), $P_O(X, Y)$, x(41), y(41) and z(41) are set and the variable I representing the position in the X direction and the variable J representing the position in the Y direction are initiated (replaced with O). Here, IM represents a picture image, X and Y are the coordinates of the picture image respectively in the X direction and Y direction, 41 is a number of divisions of the wavelength, LAB(X, Y, 3) represents the L*a*b* chromaticity space of CIE, $P_O(X, Y)$ represents the spectral composition of the observing light source and x(41), y(41) and z(41) represent equal color functions of CIE.

As a step of a picture image input, a picture image $\lambda_{380+(I-1)*10}$ corresponding to the respective wavelengths dividing the wavelength range of 380 nm to 780 nm at the intervals of 10 nm is input into the picture image input IM(X, Y, I).

Then, as steps of calculating processes, the processes of the steps shown in the following are made:
(1) I is 1-counted up.
(2) J is 1-counted up.
(3) The above mentioned first to seventh formulae are calculated.
(4) If J>Y, the process will return to (2) or, if not so, the process will move to (5).
(5) If I>X, the process will return to (1) or, if not so, the process will end.

In the above mentioned step (3), $X_O$ $Y_O$ and $Z_O$ are replaced with constants of reference white points determined by the observing light source.

The value of the CIE L*a*b* chromaticity space obtained by calculating according to the above mentioned flow chart can be output as numerical data or can be output as a video image of a quasi-color by calculating the color difference from a specific color.

Thus, according to this fifth embodiment, as the chromaticity coordinate of the observed part is calculated based on many color signals by the illuminating light of finely divided wavelength ranges and is output as data or video images, this output will become auxiliary information in objectively determining the variation of colors. Also, as the value of the chromaticity space is calculated based on the spectral characteristics, the color enhancing process by the expansion of the distribution within the space and flattening the histogram can be made at a high precision.

Also, the spectral characteristics may be calculated by using known interpolating method as the three-dimensional spline function from the spectral characteristics determined by using about eight kinds of wavelength ranges of the linear interference filter.

The equal color function of CIE is based on the sight characteristics of the human being and is not always proper to represent the distribution characteristics of hemoglobin distributed in such an ultraviolet range and infrared range as are shown in FIG. 17. Therefore, there may be a case that it is necessary to calculate a chromaticity coordinate system expanded to the ultraviolet range and infrared range. It can be easily made in this embodiment.

In the above mentioned third to fifth embodiments, an electronic endoscope of a type provided with a solid state imaging device in the tip section has been described. However, the present invention is not limited to this but can be adapted to an endoscope apparatus of a type externally fitted with a television camera wherein, as shown in FIG. 12, an image is led out of an observed object through an image guide 99 by an optical fiber or the like and is imaged by a solid state imaging device.

It is apparent that different embodiments can be formed by partly combining the above described respective embodiments.

What is claimed is:

1. A spectral distribution measuring apparatus using an endoscope comprising:
    an electronic endoscope formed of an elongate insertable section, a light guide inserted through said insertable section and emitting form another end an illuminating light input to one end surface, an objective optical system arranged on a tip side of said insertable section and an imaging means photoelectrically converting an optical image by said objective system;
    a driving means for producing a driving signal driving said imaging means;
    a light source means for sequentially outputting a light having a wavelength in a plurality of narrow bands to one end surface of said light guide, said plurality of narrow bands substantially determine a characteristic of spectral distribution by spectral measurement;
    a memory means for temporarily storing respective picture images signals imaged by said imaging means under illuminating of the light of said respective wavelengths;
    a data holding means for storing spectral data for spectral distribution calculation;
    a designating means for designating an arbitrary part of said picture image signal;
    a spectral distribution calculation means for calculating the spectral distribution of said arbitrary part from the picture image signal data stored in said memory means using said spectral data; and
    a display means for displaying a presumed spectral distribution calculated by said spectral distribution calculating means.

2. A spectral distribution measuring apparatus according to claim 1 wherein said electronic endoscope is an electronic scope in which said imaging device is arranged in a focal plane of said objective optical system.

3. A spectral distribution measuring apparatus according to claim 1 wherein said electronic endoscope is a scope externally fitted with a television camera and consisting of a fiber scope having a) an image guide arranged on one end surface in a focal plane of said objective optical system, said image guide transmitting an optical image to the other end surface and b) a television camera fitted to an eyepiece section of said fiber scope and having said imaging device built in.

4. A spectral distribution measuring apparatus according to any one of claims 1, 2 or 3 wherein when said light of said light source means is a white light, said light source means uses color transmitting filters of four or more narrow bands light of the wavelengths of said narrow bands.

5. A spectral distribution measuring apparatus according to any one of claim 1, 2, or 3 further having a second light source means illuminating with wavelengths of three different band widths covering a visible range.

6. A spectral distribution measuring apparatus according to claim 5 wherein a switch means switches said light source means and said second light source means input to said light guide.

7. A spectral distribution measuring apparatus according to claim 6 further comprising a picture image memorizing means storing respective picture image signals imaged by said imaging means illuminated by said second light source means and a signal processing means simultaneously reading out the respective picture image signals stored by said picture image memorizing means and producing a standard video signal.

8. A spectral distribution measuring apparatus according to claim 7 further having a second displaying means displaying a standard video signal output from said signal processing means.

9. A spectral distribution measuring apparatus according to claim 8 wherein said data holding means is an ROM.

10. A spectral distribution measuring apparatus according to claim 9 wherein said spectral distribution calculating means is to calculate spectral reflectivity of the respective wavelengths covering the visible light range.

11. A spectral distribution measuring apparatus according to claim 10 wherein said signal processing means has a superimposing means superimposing spectral reflectivity characteristics for the respective wavelengths calculated by said spectral distribution calculating means onto the picture image signal imaged under the illumination of said second light source means.

12. A spectral distribution measuring apparatus according to claim 11 wherein said spectral distribution calculating means has a chromaticity point calculating means displaying a chromaticity diagram on said display and a chromaticity histogram for all pixels on said chromaticity diagram.

13. A spectral distribution measuring apparatus according to any one of claims 1, 2, or 3 wherein said data holding means is an ROM.

14. A spectral distribution measuring apparatus according to claim 1 wherein a number of said narrow bands is sufficient for obtaining various amounts of photometry.

15. An endoscope apparatus comprising:

an electronic endoscope formed of an elongated insertable section, a light guide inserted though said insertable section and emitting from another end an illuminating light into to one end surface, an objective optical system arranged on a tip side of said insertable section and an imaging means photoelectrically converting an optical image by said objective optical system;

a driving means for producing a driving signal driving said imaging means;

a light source means for sequentially outputting a light having a wavelength in a plurality of narrow bands, for spectral measurement, to one end surface of said light guide;

a memory means for temporarily storing respective picture image signals of each narrow band imaged by said imaging means under illumination of the light of said respective wavelengths;

a selecting means for freely selecting the picture image signals of narrow bands of interest read out of said memory means;

a signal processing means for processing the picture image signals selected by said selecting means to produce a standard video signal; and a monitor means for displaying said standard video signal.

16. An endoscope apparatus according to claim 15 wherein said electronic endoscope is an electronic scope in which said imaging device is arranged in a focal plane of said objective optical system.

17. An endoscope apparatus according to claim 15 wherein said electronic endoscope is a scope externally fitted with a television camera and consisting of a fiber scope having a) an image guide arranged on one end surface in a focal pane of said objective optical system, said image guide transmitting an optical image to the other end surface and b) a television camera fittable to an eyepiece section of said fiber scope and having said imaging device built in.

18. An endoscope apparatus according to any one of claims 15, 16 or 17 wherein when said light of said light source means is a white light, said light source means uses color transmitting filters of four or more narrow bands to emit the light of the wavelengths of said narrow bands.

19. An endoscope apparatus according to any one of claims 15, 16 or 17 wherein said selecting means simultaneously selects three picture image signals imaged respectively in narrow wavelength ranges respectively within respective wavelength ranges of red, green and blue.

20. An endoscope apparatus according to any one of claims 15, 16 or 17 further having a calculating means for calculating at least two picture image signals read out of said memory means and for outputting them to said signal processing means.

21. An endoscope apparatus according to claim 20 wherein said calculating means has an inverse characteristic setting means making inverse characteristics.

22. An endoscope apparatus according to claim 21 wherein said calculating means has a level regulating means varying signal level by varying the gain.

23. An endoscope apparatus according to claim 22 wherein said calculating means has a logarithmic amplifier for conversion to logarithmic characteristics.

24. An endoscope apparatus according to claim 23 further having a differential amplifier obtaining a differential output of the outputs of said two logarithmic amplifiers.

25. An endoscope apparatus according to claim 24 having tow of said differential amplifiers and a divider dividing output of one differential amplifier by output of the other differential amplifier.

26. An endoscope apparatus according to claim 20 wherein said calculating means produces one of a differential signal and a divided signal for the picture image signal imaged with an illuminating light of a wavelength near 650 nm and the picture image signal imaged with an illuminating light of a wavelength near 580 nm or 800 nm.

27. An endoscope apparatus according to claim 20 wherein said calculating means makes a calculating process for the image signal of a wavelength from 600 nm to 800 nm.

28. An endoscope apparatus according to claim 20 wherein said calculating means makes a calculating process calculating a variation of light absorption rates of hemoglobin oxide and hemoglobin deoxide of the object.

* * * * *